(12) United States Patent
Alonso et al.

(10) Patent No.: US 8,735,586 B2
(45) Date of Patent: May 27, 2014

(54) REGIOSELECTIVE COPPER CATALYZED SYNTHESIS OF BENZIMIDAZOLES AND AZABENZIMIDAZOLES

(75) Inventors: Jorge Alonso, Mannheim (DE); Andreas Lindenschmidt, Frankfurt am Main (DE); Marc Nazaré, Frankfurt am Main (DE); Matthias Urmann, Frankfurt am Main (DE); Nis Halland, Frankfurt am Main (DE); Omar Rkyek, Kassel (DE)

(73) Assignee: Sanofi, Paris (FR)

( * ) Notice: Subject to any disclaimer, the term of this patent is extended or adjusted under 35 U.S.C. 154(b) by 231 days.

(21) Appl. No.: 12/644,401

(22) Filed: Dec. 22, 2009

(65) Prior Publication Data
US 2010/0261909 A1   Oct. 14, 2010

Related U.S. Application Data

(63) Continuation of application No. PCT/EP2008/004639, filed on Jun. 11, 2008.

(30) Foreign Application Priority Data

Jun. 26, 2007 (EP) .................................. 07290800

(51) Int. Cl.
*C07D 235/08* (2006.01)
*C07D 235/16* (2006.01)
*C07D 235/18* (2006.01)
*C07D 471/04* (2006.01)

(52) U.S. Cl.
CPC ............ *C07D 235/08* (2013.01); *C07D 235/16* (2013.01); *C07D 235/18* (2013.01); *C07D 471/04* (2013.01)
USPC ....................................... 546/118; 548/304.4

(58) Field of Classification Search
CPC .. C07D 235/08; C07D 235/16; C07D 235/18; C07D 471/04
USPC ........................................ 546/118; 548/304.4
See application file for complete search history.

(56) References Cited

U.S. PATENT DOCUMENTS

2007/0142448 A1*  6/2007  Hanazawa et al. ............ 514/394
2010/0197678 A1*  8/2010  Kuzmich et al. ........... 514/230.5

OTHER PUBLICATIONS

Deng et al. (Tetrahedron Lett. 45 (2004) 2311-2315.*
Klapars et al. (J. Am. Chem. Soc. 2002, 124, 7421-7428.*

* cited by examiner

*Primary Examiner* — Noble Jarrell
*Assistant Examiner* — Valerie Rodriguez-Garcia
(74) *Attorney, Agent, or Firm* — Scully, Scott, Murphy & Presser, P.C.

(57) ABSTRACT

The present invention relates to a process for the regioselective synthesis of compounds of the formula I,

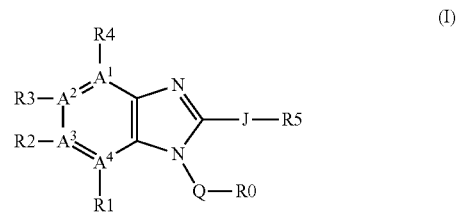

wherein R0; R1; R2; R3; R4; R5; A1; A2; A3; A4, Q and J have the meanings indicated in the claims. The present invention provides a direct copper catalyzed regioselective process to a wide variety of unsymmetrical, multifunctional N-substituted benzimidazoles or azabenzimidazoles of formula I starting from 2-halo-nitroarenes and N-substituted amides.

12 Claims, No Drawings

REGIOSELECTIVE COPPER CATALYZED SYNTHESIS OF BENZIMIDAZOLES AND AZABENZIMIDAZOLES

FIELD OF THE INVENTION

The present invention relates to a process for the regioselective synthesis of compounds of the formula I,

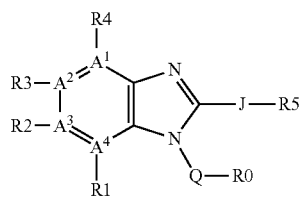

in which R0; R1; R2; R3; R4; R5; A1; A2; A3; A4, Q and J have the meanings indicated below and are useful as intermediates for the preparation of valuable pharmaceutically active ingredients.

BACKGROUND OF THE INVENTION

The present invention relates to a direct copper catalyzed, regioselective process for the preparation of a wide variety of unsymmetrical, multifunctional N-substituted benzimidazoles or azabenzimidazoles of the formula I starting from 2-halo-nitroarenes and N-substituted amides.

Benzimidazoles play an important role in drug discovery and can certainly be regarded as privileged structures in pharmaceutical research (D. A. Horton, G. T. Bourne, M. L. Smythe, Chem. Rev. 2003, 103, 893-930). The ability of this benzimidazole scaffold to mediate an interaction with a variety of biological targets, is well-documented by the multitude of reports on the observed biological activity, as well as by the fact that several benzimidazole- or azabenzimidazole-based compounds are in development or marketed as drugs and make this type of heterocycle a important element for a valuable pharmaceutically active ingredient. (W. Wienen, M. Entzeroth, J. C. A. Van Meel, J. Stangier, U. Busch, T. Ebner, J. Schmid, H. Lehmann, K. Matzek, J. Kempthorne-Rawson, V. Gladigau, N. H. Hauel, *Cardiovascular Drug Rev.* 2000, 18, 127-156; N. H. Hauel, H. Nar, H. Priepke, U. Ries, J-M. Stassen, W. Wienen, *J. Med. Chem.* 2002, 45, 1757-1766.)

Of course the use of benzimidazoles or azabenzimidazoles is not limited to the above-mentioned pharmaceutical application. For example it is well known that benzimidazoles or azabenzimidazoles can be useful in agricultural applications like for example as herbicides, fungicides, nematicidals, parasiticides, insecticides, acaricides and arthropodicides or as diagnostic agents, liquid crystals and as polymers.

In several cases, the benzimidazole or azabenzimidazoles is unsymmetrical and selectively substituted at one of the nitrogen atoms of the imidazole moiety. In contrast to the great importance of this scaffold no general regioselective route to N-substituted benzimidazoles or azabenzimidazoles has been described yet. The few methods available so far are multi-step processes often requiring harsh reaction conditions and are restricted in the substrate range, have poor cost-effectiveness and are thus of limited use (P. N. Preston, in *The Chemistry of Heterocyclic Compounds, Vol.* 40 (Eds.: A. Weissberger, E. C. Taylor), John Wiley & Sons, New York, 1981. P. L. Beaulieu, B. Haché, E. von Moos, *Synthesis* 2003, 1683-1692. D. Yang, D. Fokas, J. Li, L. Yu, C. M. Baldino, *Synthesis* 2005, 47-56; Y. M. Yutilov, *Adv. Heterocycl. Chem.*, 2005, 89, 159-270). Additionally, said processes never used compounds of formula IV for the preparation of benzimidazoles or azabenzimidazoles. Furthermore, it is surprising that copper-catalyzed reactions have hardly been used for the regioselective construction of an N-substituted benzimidazole scaffold and if so, the mentioned shortcomings were not eliminated.

Although copper-catalyzed protocols for the cross-coupling between aryl halides and amides have been reported, very few examples employing 2-halo-nitroarenes exist. Wei Deng, Ye-Feng Wang, Yan Zou, Lei Liu, Qing-Xiang Guo describe in three examples the coupling of 1-iodo-2-nitrobenzene with benzamide, N-phenylacetamide and pyrrolidine-2-one (*Tetrahedron Lett.* 2004, 45, 2311-2315) and Artis Klapars, Xiaohua Huang, Stephen L. Buchwald, describe in one example the coupling of 1-iodo-2-nitrobenzene with benzamide (*J. Am. Chem. Soc.* 2002, 124, 7421-7428). However, there is not the slightest hint in said references that the product of said processes could be used for the regioselective synthesis of benzimidazoles or azabenzimidazoles. Further no general applicability for the copper-catalyzed cross coupling of 2-halo-nitroarenes, and N-substituted amides were shown.

The limited regioselective access to N-substituted benzimidazoles or azabenzimidazoles often prevents the optimization of a potential drug substance or substance with for example agricultural application and is accompanied by poor cost-effectiveness. Thus the present invention is useful in preparing intermediates or end products of biological active compounds in pharmaceutical and agricultural applications.

SUMMARY OF THE INVENTION

The present invention provides a direct copper catalyzed, regioselective synthetic route to a wide variety of unsymmetrical, multifunctional N-substituted benzimidazoles or azabenzimidazoles of formula I starting from 2-halo-nitroarenes of formula II and substituted amides of formula III. Thus one aspect of the invention is an efficient and general copper catalyzed coupling method for substituted 2-halo-nitroarenes (step 1) to intermediates of formula IV. In another aspect of the invention, an efficient process is provided for the subsequent reductive aminocyclization (step 2) of intermediates of formula IV by using a reducing reagent. The procedure can be either performed in one pot without in-between purification of the crude reaction mixture of step 1 (one pot reaction) or optionally after simple filtration of the crude product of step 1 through a pad of celite. The economic advantage of this process is evident in avoiding purification steps, which reduce the overall waste load. The advantages of the provided process are also that it comprises a novel, direct regioselective catalytic, mild and general method for the synthesis of N-substituted benzimidazoles or azabenzimidazoles. The one-pot reaction provides a more facile access to this important scaffold class, as the process is very time- and cost-effective. Moreover, are the reaction conditions compatible with a broad range of functional groups and a large variety of starting materials, which are easily accessible or even commercially available.

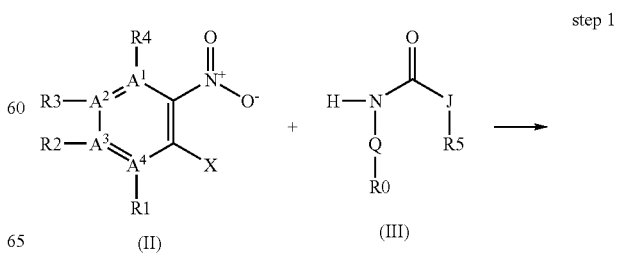

step 1

-continued

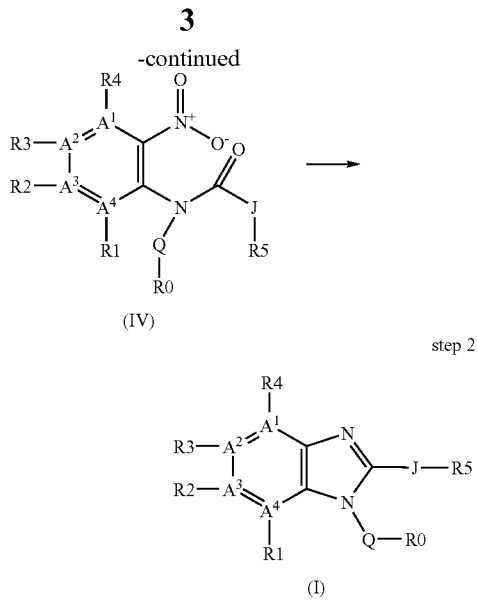

(IV)

step 2

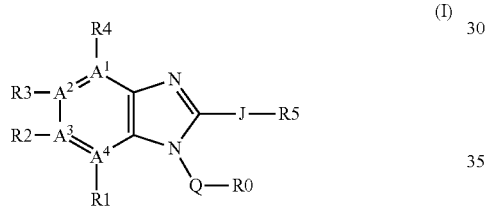

(I)

DETAILED DESCRIPTION OF THE INVENTION

A process for preparing a compound of formula I

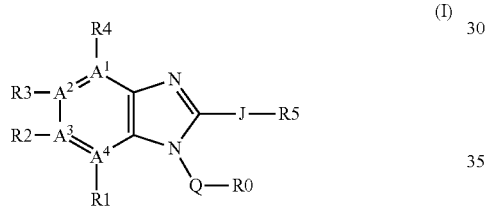

(I)

and/or all stereoisomeric forms of the compound of formula I, and/or mixtures of these forms in any ratio, and/or a physiologically tolerated salt of the compound of formula I, wherein A1, A2, A3 and A4 are independently from each other selected from a carbon or a nitrogen atom and form together with the carbon atoms they are attached to a stable aromatic or heteroaromatic ring, Q is —($C_1$-$C_6$)-alkylene, wherein alkylene is unsubstituted or mono-, di- or trisubstituted independently of one another by R14,
—($C_3$-$C_8$)-cycloalkyl, wherein cycloalkyl is unsubstituted or mono-, di- or trisubstituted independently of one another by R14,
—($C_6$-$C_{14}$)-aryl, wherein aryl is unsubstituted or mono-, di-, tri- or four times substituted independently of one another by R13; or
—($C_4$-$C_{14}$)-heteroaryl, wherein heteroaryl is unsubstituted or mono-, di-, tri- or four times substituted independently of one another by R13, J is a covalent bond,
—($C_1$-$C_6$)-alkylene, wherein alkylene is unsubstituted or mono-, di- or trisubstituted independently of one another by R14,
—($C_2$-$C_6$)-alkenylene, wherein alkenylene is unsubstituted or mono-, di- or trisubstituted independently of one another by R14,
—($C_2$-$C_6$)-alkynylene, wherein alkynylene is unsubstituted or mono-, di- or trisubstituted independently of one another by R14,
—($C_3$-$C_8$)-cycloalkyl, wherein cycloalkyl is unsubstituted or mono-, di- or trisubstituted independently of one another by R14,
—($C_6$-$C_{14}$)-aryl, wherein aryl is unsubstituted or mono-, di-, tri- or four times substituted independently of one another by R13; or
—($C_4$-$C_{14}$)-heteroaryl, wherein heteroaryl is unsubstituted or mono-, di-, tri- or four times substituted independently of one another by R13, R0, R1, R2, R3, R4 and R5 are independent of one another identical or different and are a) hydrogen atom,
b) —($C_1$-$C_4$)-alkyl, wherein alkyl is unsubstituted or substituted one to three times by R13,
c) halogen,
d) phenyloxy-, wherein phenyloxy is unsubstituted or substituted one to three times by R13,
e) —($C_1$-$C_3$)-fluoroalkyl,
f) —N(R10)-($C_1$-$C_4$)-alkyl, wherein alkyl is unsubstituted or substituted one to three times by R13,
g) —($C_9$-$C_{14}$)-aryl, wherein aryl is unsubstituted or mono-, di-, tri- or four times substituted independently of one another by R13,
h) —($C_4$-$C_{14}$)-heteroaryl, wherein heteroaryl is unsubstituted or mono-, di-, tri- or four times substituted independently of one another by R13,
i) —($C_3$-$C_8$)-cycloalkyl, wherein said cycloalkyl is unsubstituted or mono-, di-, tri- or four times substituted independently of one another by R13,
j) a 3- to 7-membered cyclic residue, containing 1, 2, 3 or 4 heteroatoms chosen from nitrogen, sulphur or oxygen, wherein said cyclic residue is unsubstituted or mono-, di-, tri- or four times substituted independently of one another by R13,
k) —O—$CF_3$,
l) —O—($C_1$-$C_4$)-alkyl, wherein alkyl is unsubstituted or substituted one to three times by R13,
m) —$NO_2$,
n) —CN,
o) —OH,
p) —C(O)—R10,
q) —C(O)—O—R11,
r) —C(O)—N(R11)-R12,
s) —N(R11)-R12,
t) —N(R10)-$SO_2$—R10,
v) —S—R10,
w) —$SO_n$—R10, wherein n is 1 or 2,
x) —$SO_2$—N(R11)-R12 or
y) at least one of R1, R2, R3 or R4 are absent in case one or more of A1, A2, A3 or A4 are nitrogen atom, or R1 and R2, R2 and R3 or R3 and R4 form together with the atoms which they are attached to a 5- or 8-membered ring, containing up to 0, 1, 2, 3 or 4 heteroatoms chosen from nitrogen, sulphur or oxygen, wherein said ring is unsubstituted or substituted one, two, three or four times by R14, R10 is hydrogen atom, —($C_1$-$C_3$)-fluoroalkyl or —($C_1$-$C_6$)-alkyl, R11 and R12 are independently of one another identical or different and are
a) hydrogen atom,
b) —($C_1$-$C_6$)-alkyl, wherein alkyl is unsubstituted or mono-, di- or trisubstituted independently of one another by R13,
c) —($C_6$-$C_{14}$)-aryl-, wherein aryl is unsubstituted or mono-, di- or trisubstituted independently of one another by R13, or d) —($C_4$-$C_{14}$)-heteroaryl, wherein heteroaryl is unsubstituted or mono-, di- or trisubstituted independently of one another by R13, R13 is halogen, —$NO_2$, —CN, =O, —OH, —($C_1$-$C_8$)-alkyl, —($C_1$-$C_8$)-alkoxy, —$CF_3$, phenyloxy-, —C(O)—R10, —C(O)—O—R17, —C(O)—N(R17)-R18, —N(R17)-R18, —N(R10)-$SO_2$—R10, —S—R10, —$SO_n$—R10, wherein n is 1 or 2, —$SO_2$—N(R17)-R18, —($C_6$-$C_{14}$)-aryl, wherein aryl is unsubstituted or mono-, di- or trisubstituted independently of one another by R14, —($C_4$-$C_{14}$)-heteroaryl, wherein heteroaryl is unsubstituted or mono-, di- or trisubstituted independently of one another by R14, —($C_3$-$C_8$)-cycloalkyl, wherein said cycloalkyl is unsubstituted or mono-, di- or trisubstituted independently of one another by R14, or a 3- to 7-membered cyclic residue, containing up to 1, 2, 3 or 4 heteroatoms chosen from nitrogen, sulphur or oxygen, wherein said cyclic residue is unsubstituted or mono-, di- or trisubstituted independently of one another by R14, R14 is halogen, —OH, =O, —CN, —$CF_3$, —($C_1$-$C_8$)-alkyl, —($C_1$-$C_4$)-alkoxy, —$NO_2$, —C(O)—OH, —$NH_2$, —C(O)—O—($C_1$-$C_4$)-alkyl, —($C_1$-$C_8$)-alkylsulfonyl, —C(O)—NH—($C_1$-$C_8$)-alkyl, —C(O)—N[($C_1$-$C_8$)-alkyl]$_2$, —C(O)—$NH_2$, —S—R10, —N(R10)-C(O)—NH—($C_1$-$C_8$)-alkyl, or —N(R10)-C(O)—N[($C_1$-$C_8$)-alkyl]$_2$, R17 and R18 are independently of one another identical or different and are a) hydrogen atom,
b) —($C_1$-$C_6$)-alkyl,
c) —($C_6$-$C_{14}$)-aryl- or
d) —($C_4$-$C_{14}$)-heteroaryl, said process comprises reacting a compound of formula II

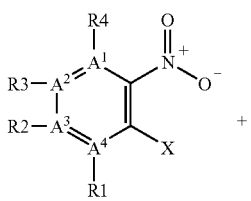

(II)

wherein R1, R2, R3 and R4 are as defined in formula I and X is Cl, Br, I, triflate or nonaflate, with a compound of formula III

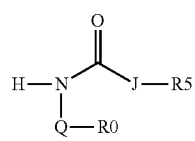

(III)

wherein Q, J, R0 and R5 are as defined in formula I, in the presence of a copper catalyst, a base, a ligand and an aprotic solvent to give a compound of formula IV

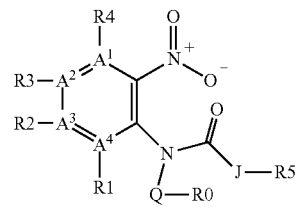

(IV)

and converting the compound of formula IV into a compound of formula I in the presence of a reducing reagent and a second solvent and optionally the compound of formula I is converted to its physiologically tolerated salt.

2) The present invention also relates to a process for the preparation of selected compounds of formula I, wherein A1, A2, A3 and A4 form together with the carbon atoms they are attached to a stable aromatic or heteroaromatic ring selected form a benzene, pyrazine, pyridazine, pyridine, pyrimidine, triazine or tetrazine, Q is —($C_1$-$C_6$)-alkylene, wherein alkylene is unsubstituted or mono-, di- or trisubstituted independently of one another by R14;

—($C_3$-$C_6$)-cycloalkyl, wherein cycloalkyl is unsubstituted or mono-, di- or trisubstituted independently of one another by R14;

phenyl, wherein phenyl is unsubstituted or mono-, di-, tri- or four times substituted independently of one another by R13; or —($C_4$-$C_{14}$)-heteroaryl, wherein heteroaryl is selected from acridinyl, azaindole (1H-pyrrolopyridinyl), azabenzimidazolyl, azaspirodecanyl, azepinyl, azetidinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyrazolo[3,4-b]pyridine, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein heteroaryl is unsubstituted or mono-, di-, tri- or four times substituted independently of one another by R13;

J is a covalent bond,
—($C_1$-$C_6$)-alkylene, wherein alkylene is unsubstituted or mono-, di- or trisubstituted independently of one another by R14;
—($C_2$-$C_6$)-alkenylene, wherein alkenylene is unsubstituted or mono-, di- or trisubstituted independently of one another by R14,
—($C_3$-$C_6$)-cycloalkyl, wherein cycloalkyl is unsubstituted or mono-, di- or trisubstituted independently of one another by R14;
phenyl, wherein phenyl is unsubstituted or mono-, di-, tri- or four times substituted independently of one another by R13; or
—($C_4$-$C_{14}$)-heteroaryl, wherein heteroaryl is as defined above and is unsubstituted or mono-, di-, tri- or four times substituted independently of one another by R13;

R0, R1, R2, R3, R4 and R5 are independent of one another identical or different and
a) hydrogen atom,
b) F,
c) Cl or Br,
d) —($C_1$-$C_4$)-alkyl, wherein alkyl is unsubstituted or substituted one to three times by R13,
e) —($C_1$-$C_3$)-fluoroalkyl,
f) phenyl, wherein phenyl is unsubstituted or substituted one to three times by R13,
g) —($C_4$-$C_{14}$)-heteroaryl, wherein heteroaryl is as defined above and is unsubstituted or mono-, di-, tri- or four times substituted independently of one another by R13,
h) —($C_3$-$C_8$)-cycloalkyl, wherein said cycloalkyl is unsubstituted or mono-, di-, tri- or four times substituted independently of one another by R13,
i) a 3- to 7-membered cyclic residue selected from azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, and is unsubstituted or mono-, di-, tri- or four times substituted independently of one another by R13,
j) —O—$CF_3$,
k) —O—($C_1$-$C_4$)-alkyl, wherein alkyl is unsubstituted or substituted one to three times by R13,
l) —N(R10)-($C_1$-$C_4$)-alkyl, wherein alkyl is unsubstituted or substituted one to three times by R13,
m) —CN,
n) —OH,
o) phenyloxy-, wherein phenyloxy is unsubstituted or substituted one to three times by R13,
p) —C(O)—O—R11,
q) —C(O)—N(R11)-R12,
r) —N(R11)-R12,
s) —N(R10)-$SO_2$—R10,
t) —S—R10,
v) —$SO_n$—R10, wherein n is 1 or 2,
w) —$SO_2$—N(R11)-R12,
x) —C(O)—R10 or
y) at least one of R1, R2, R3 or R4 are absent in case one or more of A1, A2, A3 or A4 are nitrogen atom, R10 is hydrogen atom, —($C_1$-$C_3$)-fluoroalkyl or —($C_1$-$C_6$)-alkyl, R11 and R12 are independently of one another identical or different and are
a) hydrogen atom,
b) —($C_1$-$C_4$)-alkyl, wherein alkyl is unsubstituted or mono-, di- or trisubstituted independently of one another by R13,
c) phenyl, wherein phenyl is unsubstituted or mono-, di- or trisubstituted independently of one another by R13,
d) —($C_4$-$C_{14}$)-heteroaryl, wherein heteroaryl is as defined above and is unsubstituted or mono-, di- or trisubstituted independently of one another by R13, R13 is F, Cl, —CN, =O, —OH, —($C_1$-$C_8$)-alkyl, —($C_1$-$C_8$)-alkoxy, —$CF_3$, phenyloxy-, —C(O)—R10, —C(O)—O—R17, —C(O)—N(R17)-R18, —N(R17)-R18, —N(R10)-$SO_2$—R10, —S—R10, —$SO_n$—R10, wherein n is 1 or 2, —$SO_2$—N(R17)-R18, phenyl, wherein phenyl is unsubstituted or mono-, di- or trisubstituted independently of one another by R14, —($C_4$-$C_{14}$)-heteroaryl, wherein heteroaryl is as defined above and is unsubstituted or mono-, di- or trisubstituted independently of one another by R14, —($C_3$-$C_6$)-cycloalkyl, wherein said cycloalkyl is unsubstituted or mono-, di- or trisubstituted independently of one another by R14, or a 3- to 7-membered cyclic residue, which is as defined above and is unsubstituted or mono-, di- or trisubstituted independently of one another by R14, R14 is F, Cl, —OH, =O, —CN, —$CF_3$, —($C_1$-$C_8$)-alkyl, —($C_1$-$C_4$)-alkoxy, —C(O)—OH, —$NH_2$, —C(O)—O—($C_1$-$C_4$)-alkyl, —($C_1$-$C_8$)-alkylsulfonyl, —C(O)—$NH_2$, —C(O)—NH—($C_1$-$C_8$)-alkyl, —C(O)—N[($C_1$-$C_8$)-alkyl]$_2$, —S—R10, —N(R10)-C(O)—NH—($C_1$-$C_8$)-alkyl or —N(R10)-C(O)—N[($C_1$-$C_8$)-alkyl]$_2$, R17 and R18 are independently of one another identical or different and are
a) hydrogen atom,
b) —($C_1$-$C_4$)-alkyl,
c) phenyl or
d) —($C_4$-$C_{14}$)-heteroaryl and X is Cl, Br or I.

3) The present invention also relates to a process for the preparation of compounds of formula I, wherein
A1, A2, A3 and A4 form together with the carbon atoms they are attached to a stable aromatic or heteroaromatic ring selected from benzene or pyridine,
Q is phenyl,
J is a covalent bond, —($C_1$-$C_6$)-alkylene, wherein alkylene is unsubstituted or mono-, di- or trisubstituted independently of one another by R14; phenyl or pyridyl;
R0, R1, R2, R3, R4 and R5 are independent of one another identical or different and a) hydrogen atom,
b) F,
c) Cl,
d) Br,
e) —($C_1$-$C_4$)-alkyl,
f) —O—($C_1$-$C_4$)-alkyl,
g) —C(O)—O—R11,
h) —S—R10,
i) —C(O)—R10 or
h) at least one of R1, R2, R3 or R4 are absent in case one or more of A1, A2, A3 or A4 are nitrogen atom, R10 is hydrogen atom or —($C_1$-$C_4$)-alkyl,
R11 is a) hydrogen atom, or
b) —($C_1$-$C_4$)-alkyl,
R14 is —($C_1$-$C_8$)-alkyl or —C(O)—O—($C_1$-$C_4$)-alkyl, and
X is Cl, Br or I.

The aprotic solvent useful for step 1 in the process of the present invention must be solvent, wherein the compounds of formulae II, III and IV, copper catalyst, base and ligand are soluble or at least partially soluble and compatible and is chemically inert under the reaction conditions and does not contain water or oxygen as impurities. Examples of said aprotic solvents are: benzene, toluene, xylene, mesitylene, acetonitrile, tetrahydrofurane, dimethylformamide, n-methylpyrrolodinone, dimethylacetamide, dimethylsulfoxide, (2-methoxyethyl)ether or pyridine. Preferred is benzene, mesitylene or toluene. Most preferred is toluene.

The base useful in this process of the present invention is a basic organic or inorganic compound and acts as proton acceptor without inhibiting the catalytic activity of the employed copper species or preventing the coupled intermediate species of the compound of formula IV to undergo the reductive aminocyclisation. Suitable classes of such bases are for example carbonates, phosphates, fluorides, alkoxides and hydroxides with a suitable metal as counter ion. Carbonates and phosphates are the preferred bases in the process of the present invention. Potassium carbonate or potassium phosphate and in particular caesium carbonate are the preferred bases.

The bases are generally employed in moderate excess based on the 2-halo-nitroarene of the compound of formula II. A useful range is a 1.1 to 2 fold excess based on the 2-halo-nitroarene of the compound of formula II. The base may be favourably employed in a 1.4 fold excess based on the 2-halo-nitroarene of the compound of formula I.

The copper catalyst useful in this process can be selected from the following classes: copper (I) halogen salts and copper oxides. Representative examples include, but are not limited to: copper (I) chloride, copper (I) bromide, copper (I) iodide and copper (I) oxide. The preferred catalysts is copper (I) iodide.

The copper catalyst is generally employed in an amount in the range of 0.1 to 30 mole percent based on the 2-halo-nitroarene of the compound of formula II. A useful range is 1 to 9 mole percent of copper catalyst based on the 2-halo-nitroarene of the compound of formula I.

The ligands useful in this process are mono- or bidentate amine ligands and can be selected from the following compounds: ethylenediamine, N-methylethylenediamine, N,N'-dimethyl-ethane-1,2-diamine, N,N-dimethyl-ethane-1,2-diamine N-butylethylenediamine, N,N-dimethylethylenediamine, N,N,N'-trimethylenediamine, N,N,N,N'-tetramethylenediamine, trans-1,2-cyclohexanodiamine, cis-1,2-cyclohexanodiamine, cis/trans-1,2-cyclohexanodiamine, N,N'-dimethyl-1,2-cyclohexanodiamine, N,N'-diethyl-1,2-cyclohexanodiamine, N,N'-dipropyl-1,2-cyclohexanodiamine, 1,3-propylenediamine, 1,2-benzenediamine, phenanthridine, acridine, acridine orange, 9-aminoacridine, 9-hydroxy-4-methoxyacridine, proflavine, 4-(2-pyridylazo) resorcinol, 1,2-dihydro-1-(2-(2-pyridyl)-ethyl)-3,6-pyridazinedione, [1,10]phenanthroline, 5-nitro-[1,10]phenanthroline, bathophenanthroline, spiramycin, bicinchonic acid sodium salt (bca), 1-(4-pyridyl)pyridinium chloride, 2-pyridylacetic acid hydrochloride, 8-mercapto-quinoline hydrochloride, dimethylamino acetic acid, picolinic acid, 3-hydroxypicolinic acid, 3-hydroxy picolinamide, glycol, pyridine, 2-aminopyridine, 2-hydroxypyridine, 3-cyanopyridine, 4-cyanopyridine, 2-ethylpyridine, 2-amino-6-methylpyridine, 2-(aminomethylpyridine), 2-(hydroxymethylpyridine), 2-hydroxy-6-methylpyridine, 2-dimethylaminopyridine, 4-dimethylaminopyridine, 2-(2-hydroxyethyl)-pyridine, 4-tert-butylpyridine, 3-acetoxypyridine, 2-phenylpyridine, 4-phenylpyridine, 4-benzoylpyridine, 2-(2-thienyl)pyridine, 2-benzylpyridine, 2-anilinopyridine, 3-pyridinepropanol, 1-(2-pyridyl)piperazine, di-2-pyridyl ketone, ethyl 2-pyridyl acetate, 2-(2-diethylaminoethyl)-pyridine, 4-(2-diethylaminoethyl)pyridine, 2,6-di-tert-butyl pyridine, (S,S)-2,6-bis(4-isopropyl-2-oxazolin-2-yl)pyridine, 2,3-pyridine dicarboxylic acid, 2,6-pyridine dicarboxylic acid, 3,5-pyridine dicarboxylic acid, 1,3-di(4-pyridyl)propane, 2,3-di-3-pyridyl-2,3-butanediol, 2,2'-bipyridine, 2,2-dipyridyl, 4,4'-dimethyl-2,2'-dipyridyl, 3-hydroxypyridine, 2-mercaptopyridine, 2-(2-methylaminoethyl)pyridine, 3-hydroxypicolinamine, 3-hydroxypicolinic acid, 2,2':6',2''-terpyridine, 2-picoline, 6,6'-bi-2-picoline, 2,4-lutidine, 2,6-lutidine-α-2,3-diol, 2,6-lutidine 2,4,6-collidine, picolinamide, ethyl picolinate, ethyl isonicotinate, quinoline, 2-phenylquinoline, 8-hydroxyquinoline, 8-acetoxyquinoline, 2-methyl-8-nitroquinoline, 7,8-benzoquinoline, 2-quinolinol, 2-quinolinethiol, quinoline-4-carboxylic acid, 2-phenyl-4-quinoline carboxylic acid, 2,4-hydroxyquinoline monosodium salt, 8-ethoxyquinoline-5-sulfonic acid sodium salt, 8-hydroxy-5-nitroquinoline, 4-chloro-7-(trifluoromethyl)-quinoline, 8-hydroxyquinoline-5-sulfonic acid monohydrate, 5-nitroquinaldic acid, isoquinoline, isoquinoline-3-carboxylic acid hydrate, 1,4,5-triazanaphtalene, nicotine, isonicotinamine, quinaldine, 4-chloroquinaldine, neocuproine, glycine, N-methylglycine, N,N-dimethylglycine, glycine hexyl ester, lysine, cystine, α-alanine, arginine, cysteine or β-alanine.

The most preferred ligands are trans-1,2-cyclohexanodiamine and N-methylethylenediamine.

The amine ligand is generally employed in an amount in the range of 0.1 to 60 mole percent based on the 2-halo-nitroarene of the compound of the compound of formula II. A useful range is 5 to 15 mole percent of amine ligand based on the 2-halo-nitroarene of the compound of formula II. Most favourably the amine ligand is employed in a ratio of 2 with respect to the copper source.

The reaction step 1 is carried out in the temperature range 60° C. to 150° C. A useful temperature is about 90° C. to 110° C. Generally the reaction is carried out under the exclusion of air and moisture such as under an inert atmosphere like e.g. in an argon or nitrogen atmosphere at atmospheric pressure. The reaction time for step 1 is in the range of 3 to 48 hours (h).

It is possible to filtrate or to isolate the compound of formula IV before reacting it in the second step. It is also possible to perform reaction step 2 without any separation step in the same reaction vessel.

The solvent useful for step 2 or the second solvent in the process of the present invention is an aprotic or protic solvent, wherein the compounds of formula IV or I are soluble or at least partially soluble and compatible with the reaction conditions and involved structures and reagents. Examples of said aprotic or protic solvents are: methanol, ethanol, propanol, acetic acid, methylene chloride, dimethylformamide, tetrahydrofurane, pyridine, p-xylene, ethylacetate, benzene, toluene, xylene, mesitylene or acetonitrile. Preferred are methanol, ethanol, acetic acid, methylene chloride, dimethylformamide, pyridine, p-xylene and isopropanol. Most preferred is acetic acid.

The reducing reagent useful for the reductive aminocyclization in step 2 in the process of the present invention can be selected from the following examples, but are not limited to: $H_2$/Raney-Ni, $H_2$/Pd—C, $H_2$/PtO$_2$, $H_2$/Ru, NaBH$_4$/NiCl$_2$, NaBH$_4$/FeCl$_2$, $H_3PO_2$/Pd—C, Sn/HCl, SnCl$_2$/HCl, Fe/HOAc, Fe/HCl, FeSO$_4$/HCl, Fe/FeSO$_4$, Zn/HCl, Na$_2$S, and Na$_2$S$_2$O$_4$. Favourable is Fe/HOAc as a reagent for the reductive aminocyclisation.

The reaction step 2 is carried out in the temperature range 80° C. to 140° C. A useful temperature is about 110° C. to 120° C. The reaction time for step 2 is in the range of 15 min to 120 min.

The progress of each reaction step may be monitored by methods known to those skilled in the art, like for example thin layer silica gel chromatography, gas chromatography, nuclear magnetic resonance, infrared spectroscopy, and high-pressure liquid chromatography combined with ultraviolet detection or mass spectroscopy. Preferably thin layer silica gel chromatography and high-pressure liquid chromatography (HPLC) combined with mass spectroscopy are used.

The isolation and purification procedures useful for the compounds obtained by the process of the present invention are well-known to those skilled in the art, like for example filtration through a celite containing cartridge, aqueous work-up, extraction with organic solvents, distillation, crystallisation, chromatography on silica, and high pressure liquid chromatography on normal phase or reversed phase. Preferred methods include, but are not limited to those exemplified.

Examples of "—($C_1$-$C_8$)-alkyl" or "—($C_1$-$C_8$)-alkylene" are alkyl residues containing 1, 2, 3, 4, 5, 6, 7 or 8 carbon atoms, which are e.g. methyl, methylene, ethyl, ethylene, propylene, propyl, butyl, butylene, pentyl, pentylene, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl or tert-pentyl.

Examples of "—($C_2$-$C_6$)-alkenyl" or "—($C_2$-$C_6$)-alkenylene" are alkenyls containing 2, 3, 4, 5 or 6 carbon atoms, which are e.g. vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl.

Examples of "—($C_2$-$C_6$)-alkynyl" or "—($C_2$-$C_6$)-alkynylene" are alkynyls containing 2, 3, 4, 5 or 6 carbon atoms, which are e.g. ethynyl, 1-propynyl, 2-propynyl or 2-butynyl. The term "—($C_3$-$C_8$)-cycloalkyl" is understood as cyclic alkyl residues are cycloalkyl residues containing 3, 4, 5, 6, 7 or 8 ring carbon atoms like cyclopropyl, cyclobutyl, cyclopentyl, cyclohexyl, cycloheptyl or cyclooctyl, which can also be substituted and/or unsaturated. Unsaturated cyclic alkyl groups and unsaturated cycloalkyl groups are e.g. cyclopentenyl or cyclohexenyl.

The term "A1, A2, A3, A4 are independently from each other selected from carbon or nitrogen atoms and form together with the carbon atoms they are attached to a stable aromatic or heteroaromatic ring" refers to a residue which can be derived from compounds such as benzene, pyrazine, pyridazine, pyridine, pyrimidine, triazine or tetrazine.

The term "—($C_6$-$C_{14}$)-aryl" is understood as meaning aromatic hydrocarbon radicals containing from 6 to 14 carbon atoms in the ring. Examples of —($C_6$-$C_{14}$)-aryl radicals are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals.

The term "—($C_4$-$C_{14}$)-heteroaryl" refers to mono-, di- or tri-ring systems, wherein one or more of the 4 to 14 ring carbon atoms are replaced by heteroatoms such as nitrogen, oxygen or sulfur. Examples are e.g. acridinyl, azaindole (1H-pyrrolopyridinyl), azabenzimidazolyl, azaspirodecanyl, azepinyl, azetidinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyrazolo[3,4-b]pyridine, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The term "a 3- to 7-membered cyclic residue, containing 1, 2, 3 or 4 heteroatoms" refers to structures of heterocycles, which are e.g. azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The term "R1 and R2, R2 and R3 or R3 and R4 form together with the atoms which they are attached to a 5- or 8-membered ring, containing up to 0, 1, 2, 3 or 4 heteroatoms chosen from nitrogen, sulphur or oxygen" refers to residues which are e.g. azepine, azirine, azocane, azocane-2-one, cycloheptyl, cyclohexyl, cyclooctane, cyclooctene, 1,4-diazepane, 1,2-diazepine, 1,3-diazepine, 1,4-diazepine, [1,2]diazocan-3-one, [1,3]diazocan-2-one, [1,4]diazocane, dioxazine, dioxazole, [1,4]dioxocane, 1,3-dioxolane, dioxole, 1,3-dioxolene, furan, imidazole, imidazolidine, imidazoline, isothiazole, isothiazolidine, isothiazoline, isothiazole, isoxazole, isoxazolidine, isoxazoline, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxaziridine, [1,4]oxazocane, [1,3]oxazocan-2-one, oxocane, oxocan-2-one, oxazole, piperidine, piperazine, phenyl, pyridazine, pyridine, pyrimidine, pyran, pyrazine, pyrazole, pyrazolepyrrole, pyrazolidine, pyrazoline, pyridazine, pyridine, pyrimidine, pyrrole, pyrrolidine, pyrrolidinone, pyrroline, 5,6,7,8-tetrahydro-1H-azocin-2-one, tetrahydrofuran, tetrahydropyran, tetrahydropyridine, tetrazine, tetrazole, thiadiazine, thiadiazole, 1,2-thiazine, 1,3-thiazine, 1,4-thiazine, thiazole, 1,3-thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The term "—($C_1$-$C_3$)-fluoroalkyl" is a partial or totally fluorinated alkyl-residue, which can be derived from residues such as —$CF_3$, —$CHF_2$, —$CH_2F$, —CHF—$CF_3$, —CHF—$CHF_2$, —CHF—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—CHF—$CF_3$, —$CH_2$—CHF—$CHF_2$, —$CH_2$—CHF—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —CHF—CHF—$CF_3$, —CHF—CHF—$CHF_2$, —CHF—CHF—$CH_2F$, —CHF—$CH_2$—$CF_3$, —CHF—$CH_2$—$CHF_2$, —CHF—$CH_2$—$CH_2F$, —CHF—$CF_2$—$CF_3$, —CHF—$CF_2$—$CHF_2$, —CHF—$CF_2$—$CH_2F$, —$CF_2$—CHF—$CF_3$, —$CF_2$—CHF—$CHF_2$, —$CF_2$—CHF—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

Halogen is fluorine, chlorine, bromine or iodine, preferably fluorine, chlorine or bromine, particularly preferably chlorine or bromine.

The term "triflate" refers to trifluoro-methanesulfonic acid ester or trifluoromethanesulfonate.

The term "nonaflate" refers to 1,1,2,2,3,3,4,4,4-nonafluoro-1-butanesulfonic acid ester or 1,1,2,2,3,3,4,4,4-nonafluoro-1-butanesulfonate.

The term "at least one of R1, R2, R3 or R4 are absent in case one or more of A1, A2, A3 or A4 are nitrogen atom," refers to a residue wherein the nitrogen atom is not substituted by any residue, e.g. in case A1 is nitrogen atom and A2, A3 and A4 are each a carbon atom and R4 is absent and R1, R2 and R3 are each a hydrogen atom the residue pyridine is formed. If R1, R2 and R3 are not each a hydrogen atom but one of the residues specified under b) to x) then a substituted pyridine residue is formed. In case A1 and A2 are each a nitrogen atom and A3 and A4 are each a carbon atom and R4 and R3 are absent and R1 and R2 are each a hydrogen atom the residue pyridazine is formed. If R1 and R2 are not each a hydrogen atom but one of the residues specified under b) to x) then a substituted pyridazine residue is formed.

Optically active carbon atoms present in the compounds of the formula (I) can independently of each other have R configuration or S configuration. The compounds of the formula (I) can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula (I), and it comprises all ratios of the stereoisomers in the mixtures. In case the compounds of the formula (I) can be present as E isomers or Z isomers (or cis isomers or trans isomers) the invention relates both to pure E isomers and pure Z isomers and to E/Z mixtures in all ratios. The invention also comprises all tautomeric forms of the compounds of the formula (I).

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula (I) can also be obtained by employing stereochemically uniform starting materials or by using stereoselective reactions.

The starting materials or building blocks for use in the general synthetic procedures that can be applied in the preparation of the compounds of formula (I) are readily available to one of ordinary skill in the art. In many cases they are commercially available or have been described in the literature. Otherwise they can be prepared from readily available precursor compounds analogously to procedures described in the literature, or by procedures or analogously to procedures described in this application.

Further, in order to obtain the desired substituents in the benzene nucleus and in the heterocyclic nucleus of the benzimidazole or azabenzimidazole ring system in the formula (I), the functional groups introduced into the ring system during the benzimidazole or azabenzimidazole synthesis can be chemically modified. For example, benzimidazoles carrying a hydrogen atom in the 2-position can also be obtained by oxidation of 2-methyl benzimidazole to the benzimidazole-2-carboxylic acid and subsequent decarboxylation or from benzimidazoles carrying an ester group in the respective position. Carboxylic acid groups and acetic acid groups in the 2-position can be converted into their homologues by usual reactions for chain elongation of carboxylic acids.

Especially the groups present in the benzimidazole or azabenzimidazole ring system can be modified by a variety of reactions and thus the desired residues R0, R1, R2, R3, R4 and R5 be obtained. For example, nitro groups can be reduced to amino group with under the described reaction conditions or by various reducing agents, such as sulfides, dithionites, complex hydrides or by catalytic hydrogenation. A reduction of a nitro group may also be carried out at a later stage of the synthesis of a compound of the formula (I), and a reduction of a nitro group to an amino group may also occur simultaneously with the reaction performed on another functional group, for example when reacting a group like a cyano group with hydrogen sulfide or when hydrogenating a group. Ester groups present in the benzene nucleus can be hydrolyzed to the corresponding carboxylic acids, which after activation can then be reacted with amines or alcohols under standard conditions. Ether groups present at the benzene nucleus, for example benzyloxy groups or other easily cleavable ether groups, can be cleaved to give hydroxyl groups which then can be reacted with a variety of agents, for example etherification agents or activating agents allowing replacement of the hydroxyl group by other groups. Sulfur-containing groups can be reacted analogously.

Due to the fact that in the present case the functional groups are attached to an benzimidazole or azabenzimidazole ring it may in certain cases become necessary to specifically adapt reaction conditions or to choose specific reagents from a variety of reagents that can in principle be employed into a conversion reaction, or otherwise to take specific measures for achieving a desired conversion, for example to use protection group techniques. However, finding out suitable reaction variants and reaction conditions in such cases does not cause any problems for one skilled in the art.

In the course of the preparation of the compounds of the formula I it can generally be advantageous or necessary to introduce functional groups which reduce or prevent undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, Greene and Wuts, *Protective Groups in Organic Synthesis*, Wiley, 1991, or P. Kocienski, Protecting Groups, Thieme 1994). As example of a precursor group cyano groups may be mentioned which can in a later step be transformed into carboxylic acid derivatives or by reduction into aminomethyl groups. Protective groups can also have the meaning of a solid phase, and cleavage from the solid phase stands for the removal of the protective group. The use of such techniques is known to those skilled in the art (Burgess K (Ed.) Solid Phase Organic Synthesis, New York: Wiley, 2000). For example, a phenolic hydroxyl group can be attached to a trityl-polystyrene resin, which serves as a protecting group, and the molecule is cleaved from this resin by treatment with TFA at a later stage of the synthesis. In the course of the synthesis the employment of microwave assistance for speeding-up, facilitating or enabling reactions may be beneficial or even required in many cases. Some reactions are for example described by J. L. Krstenansky, I. Cotteril, Curr. Opin. Drug. Disc. & Development., 4 (2000), 454; P. Lidstrom, J. Tierney, B. Wathey, J. Westman, Tetrahedron, 57 (2001), 9225; M. Larhed, A. Hallberg, Drug Discovery Today, 8 (2001) 406; S. Caddick, Tetrahedron, 51 (1995) 10403.

Physiologically tolerable salts of the compounds of formula I are nontoxic salts that are physiologically acceptable, in particular, pharmaceutically utilizable salts. Such salts of compounds of formula I containing acidic groups, for example, a carboxyl group (COOH), include, for example, alkali metal salts or alkaline earth metal salts, such as sodium salts, potassium salts, magnesium salts and calcium salts, as well as salts with physiologically tolerable quaternary ammonium ions, such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of formula I, for example, amino groups or guanidino groups, form acid addition salts, for example, with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I which simultaneously contain a basic group and an acidic group, for example, a guanidino group and a carboxyl group, can also be present as zwitterions (betaines) which are likewise included in the scope of the present invention.

Salts of compounds of formula I can be obtained by customary methods known to those skilled in the art, for example, by combining a compound of the formula I with an inorganic or organic acid or base in a solvent or dispersant, or from other salts by cation exchange or anion exchange. The present invention also includes all salts of the compounds of formula I which, because of low physiological tolerability, are not directly suitable for use in pharmaceuticals but are suitable, for example, as intermediates for carrying out further chemical modifications of the compounds of formula I or as starting materials for the preparation of physiologically tolerable salts.

A further aspect of the invention is the use of a compound of the formula I as prepared by the process according to the invention for the production of pharmaceuticals, diagnostic agents, liquid crystals, polymers, herbicides, fungicidals, nematicidals, parasiticides, insecticides, acaricides and arthropodicides. Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequences for preparing the compounds useful in the present invention are outlined in the examples given below. Both an explanation of, and the actual procedure for, the various aspects of the present invention are described where appropriate. Those with skill in the art will readily understand that known variations of the conditions and processes described in the examples can be used to synthesize the compounds of the present invention.

EXAMPLES

When in the final step of the synthesis of a compound an acid such as trifluoroacetic acid or acetic acid was used, for example when trifluoroacetic acid was employed to remove a tBu group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt or hydrochloric acid salt.

Abbreviations Used:

| | |
|---|---|
| Calculated | cal |
| Dimethylsulfoxide | DMSO |
| Ethylacetate | EtOAc |
| Fast atom bombardment | FAB |
| Acetic acid | HOAc |
| High pressure liquid chromatography | HPLC |
| Liquid chromatography with mass spectrometry | LC-MS |
| Melting point | mp |
| Phenyl | Ph |
| tert-Butyl | tBu |
| Trifluoroacetic acid | TFA |

Example 1

2-Methyl-1-phenyl-1H-benzimidazole

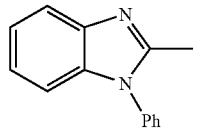 [SMILES: Cc1nc2ccccc2n1-c1ccccc1]

A reaction tube containing 2-iodonitrobenzene (125 mg, 0.5 mmol), N-phenylacetamide (81 mg, 0.6 mmol), CuI (4.8 mg, 0.025 mmol), N-methylethylenediamine (4.4 µL, 0.05 mmol), potassium phosphate (212 mg, 1 mmol) in dry toluene (3 mL) was purged with dry argon for 3 min. Then the mixture was heated at 100° C. for 18 h. After cooling, the reaction was hydrolyzed with 3 mL of water and filtered through a Varian cartridge Chem Elut 12198007, rinsing with ethyl acetate. The crude mixture was dissolved in 10 mL of glacial acetic acid and refluxed for 30 min in the presence of iron powder (279 mg, 5 mmol). The acid was removed under reduced pressure and the residue was suspended in saturated sodium bicarbonate solution and extracted with ethyl acetate. The obtained crude was purified by preparative HPLC, affording the title compound as a yellow solid (82 mg, 78% yield). mp 46-48° C. $^1$H NMR δ 2.63 (m, 3 H), 7.32 (d, J=Hz, 1 H), 7.47 (t, J=Hz, 1 H), 7.53 (t, J=Hz, 1 H), 7.66-7.72 (m, 5 H), 7.88 (d, J=7.2 Hz, 2 H); $^{13}$C NMR δ 12.6, 111.8, 115.1, 125.3, 127.1, 130.2, 130.3, 132.9, 133.8, 152.2, 158.3. HRMS (FAB): cal. for $C_{14}H_{13}N_2$ [M+H$^+$]: 209.1079; found: 209.1072. The same reaction was also performed on 25 mmol scale, obtaining the final product in 75% yield (3.9 g). The same product was obtained from 2-bromonitrobenzene (101 mg, 0.5 mmol) in 80% yield (83 mg).

Example 2

5-Chloro-2-methyl-1-phenyl-1H-benzimidazole

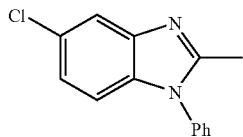 [SMILES: Cc1nc2cc(Cl)ccc2n1-c1ccccc1]

The title compound was prepared with the analogous procedure described in example 1 using 4-Chloro-1-bromo-2-nitrobenzene (118 mg, 0.5 mmol) and N-phenylacetamide (81 mg, 0.6 mmol), as starting materials to yield the title compound as yellow solid (68 mg, 56% yield). mp 109-111° C. $^1$H NMR (DMSO) δ 2.52 (s, 3 H), 7.22 (d, J=8.6 Hz, 1 H), 7.34 (d, J=8.6 Hz, 1 H), 7.48-7.59 (m, 5 H), 7.86 (s, 1 H); $^{13}$C NMR δ 13.5, 112.2, 116.4, 123.9, 126.9, 127.9, 129.7, 130.1, 133.9, 138.5, 154.0, 157.0. HRMS (FAB): cal. for $C_{14}H_{12}N_2Cl$ [M+H$^+$]: 243.0689; found: 243.0684.

Example 3

2,7-Dimethyl-1-phenyl-1H-benzimidazole

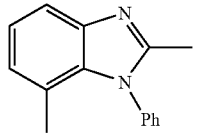 [SMILES: Cc1cccc2nc(C)n(-c3ccccc3)c12]

A reaction tube containing 2-Bromo-3-nitrotoluene (108 mg, 0.5 mmol), N-phenylacetamide (81 mg, 0.6 mmol) and trans-1,2-cyclohexanodiamine (6 µL, 0.05 mmol), potassium phosphate (212 mg, 1 mmol), copper(I) iodide (9.5 mg, 0.05 mmol) in dry toluene (3 mL) was purged with dry argon for 3 min. Then the mixture was heated at 100° C. for 18 h. After cooling, the reaction was hydrolyzed with 3 mL of water and filtered through a Varian cartridge Chem Elut 12198007, rinsing with ethyl acetate. The crude mixture was dissolved in 10 mL of glacial acetic acid and refluxed for 30 min in the presence of iron powder (279 mg, 5 mmol). The acid was removed under reduced pressure and the residue was suspended in saturated sodium bicarbonate solution and extracted with ethyl acetate. The obtained crude was purified by preparative HPLC, affording the title compound as a pale yellow solid (46 mg, 41%). mp 107-109° C. NMR (DMSO) δ 1.83 (s, 3 H), 2.34 (s, 3 H), 7.02 (d, J=7.8 Hz, 1 H), 7.22 (t, J=7.8 Hz, 1 H), 7.53 (d, J=7.8 Hz, 1 H), 7.55-7.63 (m, 5 H); $^{13}$C NMR δ 13.3, 17.1, 114.8, 121.7, 123.0, 125.5, 128.6, 129.4, 129.9, 136.0, 144.5, 151.2, 157.2. HRMS (FAB): cal. for $C_{15}H_{15}N_2$ [M+H$^+$]: 223.1235; found: 223.1231.

Example 4

5-Methoxy-2-methyl-1-phenyl-1H-benzimidazole

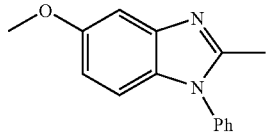

The title compound was prepared with the analogous procedure described in example 1 using 4-Iodo-3-nitroanisole (140 mg, 0.5 mmol) and N-phenylacetamide (81 mg, 0.6 mmol) as starting materials to yield the title compound as a pale yellow solid (80 mg, 67%). mp 88-90° C. $^1$H NMR (DMSO) δ 2.61 (s, 3 H), 3.88 (s, 3 H), 7.07 (d, J=8.9 Hz, 1 H), 7.25 (d, J=8.9 Hz, 1 H), 7.38 (br s, 1 H), 7.65-7.73 (m, 5 H); $^{13}$C NMR δ 12.5, 55.9, 97.7, 112.6, 114.7, 126.9, 127.8, 130.2, 130.3, 132.8, 133.1, 151.2, 157.6, 157.8. HRMS (FAB): cal. for $C_{15}H_{15}N_2O$ [M+H$^+$]: 239.1184; found: 239.1180.

Example 5

2-Methyl-1-phenyl-1H-benzimidazole-5-carboxylic acid methyl ester

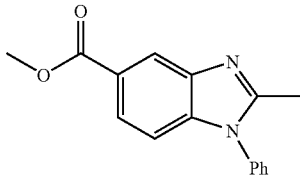

The title compound was prepared with the analogous procedure described in example 1 using 4-Bromo-3-nitrobenzoic acid methyl ester (130 mg, 0.5 mmol) and N-phenylacetamide (81 mg, 0.6 mmol) as starting materials to yield the title compound as colorless crystals (78 mg, 59%). mp 108-110° C. $^1$H NMR (DMSO) δ 2.55 (s, 3 H), 3.78 (s, 3 H), 7.30 (d, J=8.2 Hz, 1 H), 7.52-7.71 (m, 5 H), 7.92 (d, J=8.2 Hz, 1 H), 8.30 (br s, 1 H); $^{13}$C NMR δ 13.6, 52.1, 110.8, 118.5, 124.7, 124.8, 127.0, 129.7, 130.1, 134.0, 137.9, 153.7, 157.8, 166.2. HRMS (FAB): cal. for $C_{16}H_{15}N_2O_2$ [M+H]$^+$: 267.1134; found: 267.1128.

Example 6

2-Methyl-1-phenyl-1H-benzimidazole-5-carbaldehyde

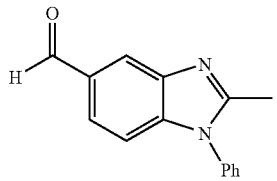 [SMILES: Cc1nc2cc(C=O)ccc2n1-c1ccccc1]

The title compound was prepared with the analogous procedure described in example 3 using 4-Dimethoxymethyl-1-iodo-2-nitrobenzene (155 mg, 0.5 mmol) and N-phenylacetamide (81 mg, 0.6 mmol) as starting materials to yield the title compound as pale yellow oil (30 mg, 25% yield). $^1$H NMR (DMSO) δ 2.50 (s, 3 H), 7.31 (d, J=8.3 Hz, 1 H), 7.61-7.68 (m, 5 H), 7.82 (d, J=8.3 Hz, 1 H), 8.25 (s, 1 H), 10.10 (s, 1 H); $^{13}$C NMR δ 13.6, 111.4, 120.1, 124.2, 127.0, 129.8, 130.2, 132.3, 139.1, 154.7, 158.3, 192.4. HRMS (FAB): cal. for $C_{15}H_{13}N_2O$ [M+H]$^+$: 237.1028; found: 237.1024.

Example 7

1,2-Diphenyl-1H-benzimidazole

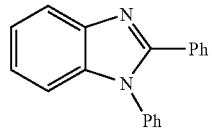 [SMILES: c1ccc(-c2nc3ccccc3n2-c2ccccc2)cc1]

a) Two step process

The title compound was prepared with the analogous procedure described in example 1 using 1-Iodo-2-nitrobenzene (125 mg, 0.5 mmol) and benzanilide (118 mg, 0.6 mmol) as starting materials to yield the title compound as pale yellow solid (95 mg, 70%). mp 105-107° C. $^1$H NMR (DMSO) δ 7.24 (d, J=7.9 Hz, 1 H), 7.35-7.62 (m, 12 H), 7.84 (d, J=7.6 Hz, 1 H); $^{13}$C NMR δ 111.0, 118.1, 123.7, 124.1, 127.5, 127.9, 128.4, 129.2, 129.3, 130.0, 130.2, 135.5, 136.2, 139.3, 151.3. HRMS (FAB): cal. for $C_{19}H_{15}N_2$ [M+H]$^+$: 271.1235; found: 271.1230.

b) One Pot Reaction

A reaction tube containing 1-iodo-2-nitrobenzene (124 mg, 0.5 mmol), N-phenylbenzamide (118 mg, 0.6 mmol), CuI (4.8 mg, 0.025 mmol), N-methylethylenediamine (4.4 µL, 0.05 mmol), potassium phosphate (212 mg, 1 mmol) in dry toluene (1.5 mL) was purged with dry argon for 3 min. After heating at 100° C. for 18 h, the iron powder (10 mol.-eq.) and glacial acetic acid (5 mL) are directly added. Then the reaction mixture is heated at reflux for 30 min. An additional 10 mol.-eq. of iron powder are added and the reaction mixture is heated at reflux for further 30 min. The solvents were removed under reduced pressure and the crude was extracted with ethyl acetate against saturated sodium bicarbonate solution. The organic phase was dried and the solvent was removed on a rotary evaporator. Then the residue was purified by preparative HPLC, affording the title compound as a solid (90 mg, 67% yield).

Example 8

1-Phenyl-2-pyridin-3-yl-1H-benzimidazole

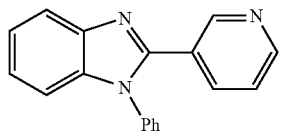 [SMILES: c1ccc(-n2c(-c3cccnc3)nc3ccccc32)cc1]

The title compound was prepared with the analogous procedure described in example 1 using 1-Iodo-2-nitrobenzene (125 mg, 0.5 mmol) and nicotinanilide (119 mg, 0.6 mmol) as starting materials to yield the title compound as brown solid (91 mg, 67%). mp 110-112° C. $^1$H NMR (DMSO) δ 7.26 (d, J=7.3 Hz, 1 H), 7.32-7.63 (m, 8 H), 7.86 (d, J=7.6 Hz, 1 H), 7.89 (d, J=7.8 Hz, 1 H), 8.62 (d, J=3.0 Hz, 1 H), 8.72 (br s, 1 H); $^{13}$C NMR δ 111.0, 118.7, 123.8, 124.0, 124.4, 125.4, 127.6, 129.5, 130.2, 135.2, 136.4, 137.7, 140.3, 148.6, 149.6, 158.3. HRMS (FAB): cal. for $C_{18}H_{14}N_3$ [M+H]$^+$: 272.1188; found: 272.1180.

Example 9

1-Phenyl-2-tridecyl-1H-benzimidazole

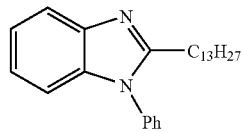

The title compound was prepared with the analogous procedure described in example 1 using 1-Iodo-2-nitrobenzene (125 mg, 0.5 mmol) and myristanilide (182 mg, 0.6 mmol) as starting materials to yield the title compound as colorless oil (160 mg, 85%). $^1$H NMR (DMSO) δ 0.74 (t, J=6.9 Hz, 3 H), 1.14-1.28 (m, 20 H), 1.68 (p, J=7.6 Hz, 2 H), 2.83 (t, J=7.6 Hz, 2 H), 7.14 (d, J=8.1 Hz, 1 H), 7.29 (dd, J=8.1, 7.7 Hz, 1 H), 7.47 (dd, J=8.1, 7.7 Hz, 1 H), 7.56-7.68 (m, 5 H), 7.74 (d, J=7.7 Hz, 1 H); $^{13}$C NMR δ 13.9, 22.0, 26.3, 26.4, 28.3, 28.4, 28.7, 28.8, 28.9, 29.9, 31.2, 110.7, 116.9, 123.5, 123.7, 127.2, 129.6, 130.1, 134.2, 135.0, 137.6, 154.7. HRMS (FAB): cal. for C$_{26}$H$_{36}$N$_2$ [M+H$^+$]: 377.2957; found: 377.2953.

Example 10

5-(1-Phenyl-1H-benzoimidazol-2-yl)-pentanoic acid methyl ester

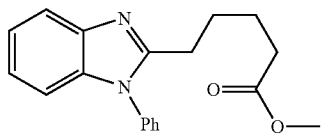

The title compound was prepared with the analogous procedure described in example 1 using 1-Iodo-2-nitrobenzene (125 mg, 0.5 mmol) and 5-phenylcarbamoyl-pentanoic acid methyl ester (141 mg, 0.6 mmol) as starting materials to yield the title compound as brown oil (66 mg, 43%). $^1$H NMR (DMSO) δ 1.50-1.74 (m, 4 H), 2.27 (d, J=7.2 Hz, 2 H), 2.89 (d, J=7.5 Hz, 2 H), 3.52 (s, 3 H), 7.22 (d, J=8.1 Hz, 1 H), 7.38 (apparent t, J=7.6 Hz, 1 H), 7.46 (apparent t, J=7.6 Hz, 1 H), 7.52-7.72 (m, 5 H), 7.79 (d, J=7.8 Hz, 1 H); $^{13}$C NMR δ 23.3, 25.3, 25.4, 32.2, 50.9, 111.3, 115.6, 124.3, 124.4, 126.8, 130.0, 132.4, 133.2, 133.4, 153.9, 172.3. HRMS (FAB): cal. for C$_{19}$H$_{21}$N$_2$O$_2$ [M+H$^+$]: 309.1603; found: 309.1595.

Example 11

1-(4-Methoxyphenyl)-2-methyl-1H-benzimidazole

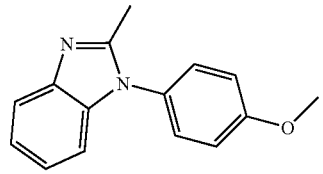 [SMILES: COc1ccc(-n2c(C)nc3ccccc32)cc1]

The title compound was prepared with the analogous procedure described in example 1 using 1-Iodo-2-nitrobenzene (125 mg, 0.5 mmol) and p-acetanisidide (99 mg, 0.6 mmol) as starting materials to yield the title compound as colorless solid (86 mg, 72%). mp 121-123° C. $^1$H NMR (DMSO) δ 2.61 (s, 3 H), 3.87 (s, 3 H), 7.23 (d, J=9.1 Hz, 2 H), 7.28 (d, J=8.7 Hz, 1 H), 7.52 (dd, J=8.1, 7.4 Hz, 1 H), 7.48 (dd, J=7.8, 7.4 Hz, 1 H), 7.59 (d, J=9.1 Hz, 2 H), 7.83 (d, J=7.8 Hz, 1 H); $^{13}$C NMR δ 12.6, 55.6, 111.7, 115.1, 115.3, 125.1, 125.3, 128.4, 132.5, 134.1, 152.3, 158.2, 160.2. HRMS (FAB): cal. for C$_{15}$H$_{15}$N$_2$O [M+H$^+$]: 239.1184; found: 239.1179.

Example 12

2,4-Dimethyl-1-phenyl-1H-benzimidazole

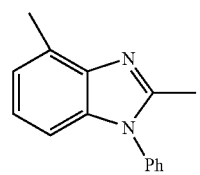 [SMILES: Cc1cccc2c1nc(C)n2-c1ccccc1]

The title compound was prepared with the analogous procedure described in example 1 using 3-Bromo-2-nitrotoluene (108 mg, 0.5 mmol) and N-phenylacetamide (81 mg, 0.6 mmol), as starting materials to yield the title compound as brown solid (37 mg, 33%). $^1$H NMR (DMSO) δ 2.46 (s, 3 H), 2.55 (s, 3 H), 6.88 (d, J=7.3 Hz, 1 H), 7.04-7.11 (m, 2 H), 7.50-7.64 (m, 5 H); $^{13}$C NMR δ 13.8, 16.3, 107.5, 122.5, 122.6, 126.8, 129.9, 135.1, 135.3, 150.3, 158.3.

Example 13

1-(2-Methoxy-phenyl)-2-methyl-1H-benzoimidazole

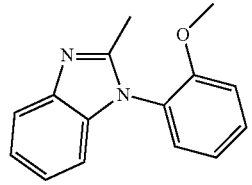 [SMILES: COc1ccccc1-n1c(C)nc2ccccc21]

The title compound was prepared with the analogous procedure described in example 1 using 1-Iodo-2-nitrobenzene (124 mg, 0.5 mmol) and N-(2-methoxyphenyl)-acetamide (99 mg, 0.6 mmol) as starting materials to yield the title compound as a yellow solid (60 mg, 50%). $^1$H NMR (DMSO) δ 2.29 (s, 3 H), 3.73 (s, 3 H), 6.88 (d, J=8.1 Hz, 1 H), 7.08-7.18 (m, 3 H), 7.31 (d, J=7.6 Hz, 1 H), 7.41 (d, J=7.9 Hz, 1 H), 7.54-7.58 (m, 2 H); $^{13}$C NMR δ 13.5, 55.6, 109.6, 112.9, 118.2, 121.0, 121.5, 121.9, 123.5, 129.0, 130.7, 136.2, 142.4, 151.9, 154.6.

Example 14

1-(2-Chloro-phenyl)-2-methyl-1H-benzoimidazole

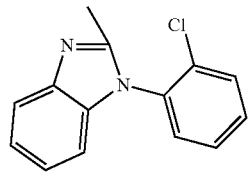 [SMILES: Cc1nc2ccccc2n1-c1ccccc1Cl]

The title compound was prepared with the analogous procedure described in example 1 using 1-Iodo-2-nitrobenzene (124 mg, 0.5 mmol) and N-(2-chlorophenyl)-acetamide (102 mg, 0.6 mmol) as starting materials to yield the title compound as a yellow solid (74 mg, 61%). $^1$H NMR (DMSO) δ 2.63 (s, 3 H), 7.34 (d, J=7.9 Hz, 1 H), 7.41 (t, J=7.9 Hz, 1 H), 7.48 (t, J=7.9 Hz, 1 H), 7.64 (d, J=8.6 Hz, 2 H), 7.82 (d, J=7.9 Hz, 1 H), 7.92 (d, J=8.6 Hz, 2 H).

Example 15

2-Methyl-1-(4-methylsulfanylphenyl)-1H-benzoimidazole

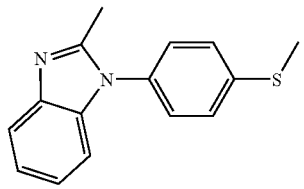 [SMILES: CSc1ccc(-n2c(C)nc3ccccc32)cc1]

The title compound was prepared with the analogous procedure described in example 1 using 1-Iodo-2-nitrobenzene (124 mg, 0.5 mmol) and N-(4-methylsulfanylphenyl)-acetamide (109 mg, 0.6 mmol) as starting materials to yield the title compound as a yellow solid (74 mg, 58%). $^1$H NMR (DMSO) δ 2.58 (s, 3 H), 2.64 (s, 3 H), 7.37 (d, J=8.1 Hz, 1 H), 7.44 (dd, J=8.1, 7.3 Hz, 1 H), 7.48-7.52 (m, 1 H), 7.54 (d, J=8.8 Hz, 2 H), 7.61 (d, J=8.8 Hz, 2 H), 7.86 (d, J=7.3 Hz, 1 H); $^{13}$C NMR δ 12.6, 14.3, 111.8, 115.1, 125.2, 126.7, 127.5, 129.3, 132.7, 133.8, 141.5, 152.2, 158.2.

Example 16

1-(4-Bromo-phenyl)-2-methyl-1H-benzoimidazole

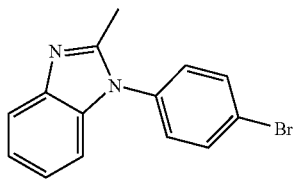 [SMILES: Cc1nc2ccccc2n1-c1ccc(Br)cc1]

The title compound was prepared with the analogous procedure described in example 1 using 1-Iodo-2-nitrobenzene (124 mg, 0.5 mmol) and N-(4-bromophenyl)-acetamide (128 mg, 0.6 mmol) as starting materials to yield the title compound as a yellow solid (109 mg, 76%). $^1$H NMR (DMSO) δ 2.63 (s, 3 H), 7.34 (d, J=7.9 Hz, 1H), 7.41 (t, J=7.9 Hz, 1 H), 7.48 (t, J=7.9 Hz, 1 H), 7.64 (d, J=8.6 Hz, 2 H), 7.82 (d, J=7.9 Hz, 1 H), 7.92 (d, J=8.6 Hz, 2 H); $^{13}$C NMR δ 12.8, 111.7, 115.4, 123.6, 125.1, 125.2, 129.3, 132.5, 133.3, 134.5, 152.8, 157.6.

Example 17

2,4-Dimethyl-1-phenyl-1H-benzoimidazole-5-carboxylic acid methyl ester

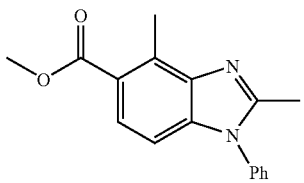

The title compound was prepared with the analogous procedure described in example 3 using 4-Bromo-2-methyl-3-nitrobenzoic acid methyl ester and N-phenylacetamide (81 mg, 0.6 mmol) as starting materials to yield the title compound as yellow solid. $^1$H NMR (DMSO) δ 2.49 (s, 3 H), 2.62 (s, 3 H), 7.18 (d, J=8.6 Hz, 1 H), 7.28 (d, J=8.6 Hz, 1 H), 7.52-7.61 (m, 6 H); $^{13}$C NMR δ 13.5, 14.7, 51.8, 108.0, 123.7, 125.9, 126.9, 129.7, 130.1, 130.2, 134.0, 136.5, 138.0, 152.8, 167.2.

Example 18

5-Fluoro-2-methyl-1-phenyl-1H-benzoimidazole

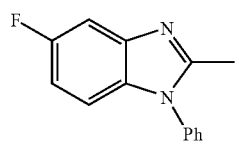

The title compound was prepared with the analogous procedure described in example 3 using 1-Bromo-4-fluoro-2-nitrobenzene and N-phenylacetamide (81 mg, 0.6 mmol) as starting materials to yield the title compound as brown solid (69 mg, 61%). $^1$H NMR (DMSO) δ 2.49 (s, 3 H), 7.17-7.32 (m, 2 H), 7.61-7.73 (m, 6 H).

Example 19

5-Bromo-2-methyl-1-phenyl-1H-benzoimidazole

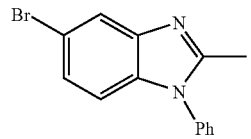

The title compound was prepared with the analogous procedure described in example 1 using 2,5-Dibromonitrobenzene (140 mg, 0.5 mmol) and N-phenylacetamide (81 mg, 0.6 mmol) as starting materials to yield the title compound as a yellow solid (87 mg, 61%). $^1$H NMR (DMSO) δ 2.52 (s, 3 H), 7.18 (d, J=8.8 Hz, 1 H), 7.43 (d, J=8.8 Hz, 1 H), 7.58-7.68 (m, 5 H), 7.98 (br s, 1 H); $^{13}$C NMR δ 13.5, 112.5, 115.5, 119.5, 126.4, 126.9, 129.6, 130.1, 134.0, 139.0, 154.2, 156.8.

Example 20

1-(2-Methyl-1-phenyl-1H-benzoimidazol-5-yl)-ethanone

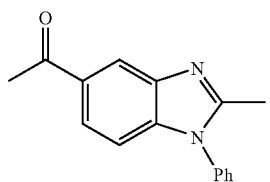 [SMILES: CC(=O)c1ccc2c(c1)nc(C)n2-c1ccccc1]

The title compound was prepared with the analogous procedure described in example 1 using 1-(4-Bromo-3-nitrophenyl)-ethanone (122 mg, 0.5 mmol) and N-phenylacetamide (81 mg, 0.6 mmol) as starting materials to yield the title compound as a yellow solid (78 mg, 62%). $^1$H NMR (DMSO) δ 2.54 (s, 3 H), 2.68 (s, 3 H), 7.27 (d, J=8.6 Hz, 1 H), 7.58-7.71 (m, 5 H), 7.92 (d, J=8.86 Hz, 1 H), 8.35 (br s, 1 H); $^{13}$C NMR δ 13.8, 27.0, 110.4, 117.9, 123.5, 126.7, 129.7, 130.0, 132.4, 133.9, 137.9, 153.8, 157.2, 197.0.

Example 21

6-Fluoro-2-methyl-1-phenyl-1H-benzoimidazole

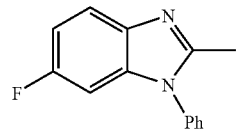

The title compound was prepared with the analogous procedure described in example 3 using 1-Bromo-5-fluoro-2-nitrobenzene and N-phenylacetamide (81 mg, 0.6 mmol) as starting materials to yield the title compound as brown solid (75 mg, 66%). $^1$H NMR (DMSO) δ 2.50 (s, 3 H), 7.11 (d, 1 H), 7.21-7.29 (m, 1H), 7.59-7.69 (m, 5 H), 7.79 (br s, 1 H).

Example 22

1-Phenyl-1H-benzoimidazole

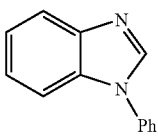

a) Two Step Process

The title compound was prepared with the analogous procedure described in example 1 using 1-Iodo-2-nitrobenzene (124 mg, 0.5 mmol) and N-Phenyl-formamide (73 mg, 0.6 mmol) as starting materials to yield the title compound as a yellow solid (70 mg, 72%). $^1$H NMR (DMSO) δ 7.28-7.33 (m, 2 H), 7.49 (d, J=7.3 Hz, 1 H), 7.59-7.68 (m, 5 H), 7.79 (d, J=6.9 Hz, 1 H), 8.56 (br s, 1 H); $^{13}$C NMR δ 110.6, 119.9, 122.4, 123.6, 123.9, 127.6, 130.0, 133.1, 135.9, 143.8.

b) One Pot Reaction

The title compound was prepared with the analogous procedure described in example 7 (one pot reaction) using 1-iodo-2-nitrobenzene (124.5 mg, 0.5 mmol) and N-phenyl-formamide (73 mg, 0.6 mmol) as starting materials to yield the title compound as a yellow solid (70 mg, 72%).

Example 23

6-Methoxy-1-phenyl-1H-benzimidazole

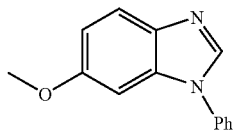 [SMILES: COc1ccc2ncn(-c3ccccc3)c2c1]

The title compound was prepared with the analogous procedure described in example 1 using 2-Iodo-4-methoxy-1-nitrobenzene (140 mg, 0.5 mmol) and N-Phenyl-formamide (73 mg, 0.6 mmol) as starting materials to yield the title compound as viscous oil (62 mg, 56%). $^1$H NMR (DMSO) δ 2.58 (s, 3 H), 2.64 (s, 3 H), 7.37 (d, J=8.1 Hz, 1 H), 7.44 (dd, J=8.1, 7.3 Hz, 1 H), 7.48-7.52 (m, 1 H), 7.54 (d, J=8.8 Hz, 2 H), 7.61 (d, J=8.8 Hz, 2 H), 7.86 (d, J=7.3 Hz, 1 H).

Example 24

2-Methyl-3-phenyl-3H-benzoimidazole-4-carboxylic acid methyl ester

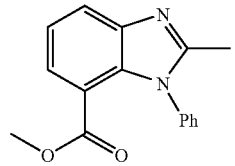

The title compound was prepared with the analogous procedure described in example 3 using 2-Bromo-3-nitrobenzoic acid methyl ester and N-phenylacetamide (81 mg, 0.6 mmol) as starting materials to yield the title compound as viscous oil (40 mg, 30%). $^1$H NMR (DMSO) δ 2.41 (s, 3 H), 3.08 (s, 3 H), 7.39-7.63 (m, 7 H), 7.96 (br s, 1 H); $^{13}$C NMR δ 14.1, 51.8, 117.2, 121.1, 123.0, 124.9, 137.0, 139.3, 139.6, 137.0, 140.2, 155.2, 165.7.

Example 25

2-Methyl-1-phenyl-1H-imidazo[4,5-b]pyridine

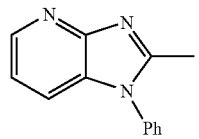 [SMILES: Cc1nc2ncccc2n1-c1ccccc1]

The title compound was prepared with the analogous procedure described in example 3 using 3-Bromo-2-nitropyridine (101 mg, 0.5 mmol) and N-phenylacetamide (81 mg, 0.6 mmol) as starting materials to yield the title compound as brown viscous oil (49 mg, 47% yield). $^1$H NMR (DMSO) δ 2.54 (s, 3 H), 7.35-7.68 (m, 6 H), 7.77 (d, J=8.8 Hz, 1 H), 8.58 (br s, 1 H); $^{13}$C NMR δ 14.0, 118.9, 120.1, 126.8, 128.5, 129.6, 130.1, 133.9, 143.0, 151.6, 156.7. HRMS (FAB): cal. for $C_{13}H_{12}N_3$ [M-FH$^+$]: 210.1031; found: 210.1026.

Example 26

2-Methyl-3-phenyl-3H-imidazo[4,5-b]pyridine

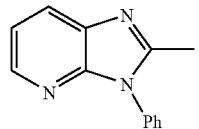 [SMILES: Cc1nc2cccnc2n1-c1ccccc1]

The title compound was prepared with the analogous procedure described in example 3 using 2-Bromo-3-nitropyridine (101 mg, 0.5 mmol) and N-phenylacetamide (81 mg, 0.6 mmol) as starting materials to yield the title compound as pale yellow viscous oil (55 mg, 53%). $^1$H NMR (DMSO) δ 2.48 (s, 3 H), 7.24 (dd, 1 H), 7.53-7.63 (m, 5 H), 8.02 (d, 1 H), 8.20 (d, 1 H); $^{13}$C NMR δ 14.6, 118.3, 125.9, 127.4, 128.7, 129.3, 134.1, 134.3, 143.0, 148.7, 152.9. HRMS (FAB): cal. for $C_{13}H_{12}N_3$ [M-FH$^+$]: 210.1031; found: 210.1027.

Example 27

5-Methoxy-2-methyl-3-phenyl-3H-imidazo[4,5-b]pyridine

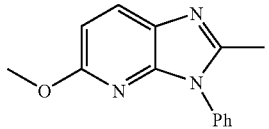

The title compound was prepared with the analogous procedure described in example 3 using 2-Bromo-6-methoxy-3-nitropyridine (116 mg, 0.5 mmol) and N-phenylacetamide (81 mg, 0.6 mmol) as starting materials to yield the title compound as pale yellow solid (112 mg, 94%). mp 114-116° C. $^1$H NMR (DMSO) δ 2.56 (s, 3 H), 3.76 (s, 3 H), 6.85 (d, J=8.6 Hz, 1 H), 7.53-7.68 (m, 5 H), 8.12 (d, J=8.6 Hz, 1 H). $^{13}$C NMR δ 13.8, 53.4, 107.7, 122.9, 127.0, 128.0, 128.4, 129.2, 132.6, 144.1, 150.3, 161.1. HRMS (FAB): cal. for C$_{14}$H$_{14}$N$_3$O [M-FH$^+$]: 240.1237; found: 240.1234.

Example 28

2,5-Dimethyl-3-phenyl-3H-imidazo[4,5-b]pyridine

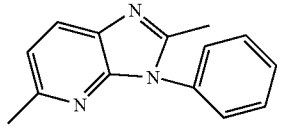 [SMILES: Cc1ccc2nc(C)n(-c3ccccc3)c2n1]

The title compound was prepared with the analogous procedure described in example 3 using 2-Bromo-6-methyl-3-nitropyridine (108 mg, 0.5 mmol) and N-phenylacetamide (81 mg, 0.6 mmol) as starting materials to yield the title compound as brown viscous oil (57 mg, 51%). $^1$H NMR (DMSO) δ 2.42 (s, 3 H), 3.31 (s, 3 H), 7.11 (d, J=8.0 Hz, 1 H), 7.51-7.63 (m, 5 H), 7.89 (d, J=8.0 Hz, 1 H); $^{13}$C NMR δ 14.6, 23.8, 118.0, 126.1, 127.7, 128.7, 129.4, 132.1, 134.8, 148.3, 150.9, 151.1. HRMS: cal for C$_{14}$H$_{14}$N$_3$ [M+H$^+$]: 224.1188; found: 224.1184.

Example 29

3-(1-Phenyl-1H-benzimidazol-2-yl)-propionic acid ethyl ester

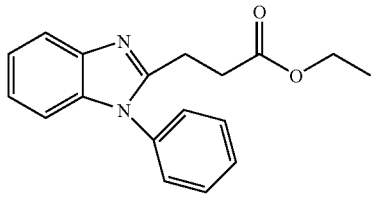 [SMILES: CCOC(=O)CCc1nc2ccccc2n1-c1ccccc1]

The title compound was prepared with the analogous procedure described in example 7 (one pot reaction) using 1-iodo-2-nitrobenzene (124.5 mg, 0.5 mmol) and 4-phenyl-carbamoyl-butyric acid ethyl ester (133 mg, 0.6 mmol) as starting materials to yield the title compound as a solid (68 mg, 46%). $^1$H NMR (DMSO) δ 1.12 (t, 3H), 2.88 (t, 2H), 3.10 (t, 2H), 4.03 (q, 2H), 7.21 (d, 1H), 7.39 (m, 2H), 7.65 (m, 2 H), 7.72 (m, 3H), 7.78 (d, 1 H). [M+H$^+$]: 295.15.

Example 30

1-(2-Chloro-phenyl)-2-((E)-styryl)-1H-benzimidazole

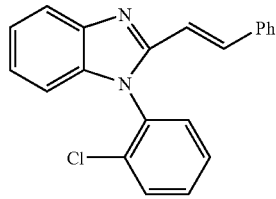 [SMILES: Clc1ccccc1-n1c(/C=C/c2ccccc2)nc2ccccc21]

The title compound was prepared with the analogous procedure described in example 7 (one pot reaction) using 1-iodo-2-nitrobenzene (124.5 mg, 0.5 mmol) and N-(2-chloro-phenyl)-3-phenylacrylamide (154 mg, 0.6 mmol) as starting materials to yield the title compound as a solid (35 mg, 21%). $^1$H NMR (DMSO) δ 6.73 (d, 1 H), 7.03 (d, 1H), 7.31 (t, 1H), 7.39 (m, 4H), 7.58 (d, 2 H), 7.70 (m, 1H), 7.75 (m, 1H), 7.79 (m, 2H), 7.88 (dd, 2H). [M+H$^+$]: 331.08.

The invention claimed is:
1. A process for preparing a compound of formula I

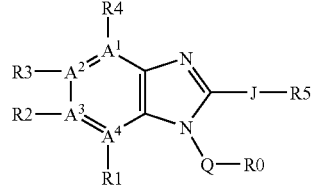

(I)

or all stereoisomeric forms of the compound of formula I, or mixtures of these forms in any ratio, or a physiologically tolerated salt of the compound of formula I, wherein A1, A2, A3 and A4 are independently from each other selected from the group consisting of carbon and nitrogen atoms and form together with the carbon atoms they are attached to a stable aromatic or heteroaromatic ring, with the provisos that if A1 is N then R4 is absent; if A2 is N then R3 is absent; if A3 is N then R2 is absent; and if A4 is N then R1 is absent;

Q is —(C$_1$-C$_6$)-alkylene, wherein alkylene is unsubstituted or mono-, di- or trisubstituted independently of one another by R14;

—(C$_3$-C$_8$)-cycloalkyl, wherein cycloalkyl is unsubstituted or mono-, di- or trisubstituted independently of one another by R14;

—(C$_6$-C$_{14}$)-aryl, wherein aryl is unsubstituted or mono-, di-, tri- or four times substituted independently of one another by R13: or —(C$_4$-C$_{14}$)-heteroaryl, wherein heteroaryl is unsubstituted or mono-, di-, tri- or four times substituted independently of one another by R13;

J is a covalent bond,
—(C$_1$-C$_6$)-alkylene, wherein alkylene is unsubstituted or mono-, di- or trisubstituted independently of one another by R14;

—(C$_2$-C$_6$)-alkenylene, wherein alkenylene is unsubstituted or mono-, di- or trisubstituted independently of one another by R14, —(C$_2$-C$_6$)-alkynylene, wherein alkynylene is unsubstituted or mono-, di- or trisubstituted independently of one another by R14, —(C$_3$-C$_8$)-cycloalkyl, wherein cycloalkyl is unsubstituted or mono-, di- or trisubstituted independently of one another by R14;

—(C$_6$-C$_{14}$)-aryl, wherein aryl is unsubstituted or mono-, di-, tri- or four times substituted independently of one another by R13: or —(C$_4$-C$_{14}$)-heteroaryl, wherein heteroaryl is unsubstituted or mono-, di-, tri- or four times substituted independently of one another by R13;

R0, R1, R2, R3, R4 and R5 are independent of one another identical or different and are a) hydrogen atom, b) —(C$_1$-C$_4$)-alkyl, wherein alkyl is unsubstituted or substituted one to three times by R13, c) halogen, d) phenyloxy-, wherein phenyloxy is unsubstituted or substituted one to three times by R13, e) —(C$_1$-C$_3$)-fluoroalkyl, f) —N(R10)-(C$_1$-C$_4$)-alkyl, wherein alkyl is unsubstituted or substituted one to three times by R13, g) —($C_6$-$C_{14}$)-aryl, wherein aryl is unsubstituted or mono-, di-, tri- or four times substituted independently of one another by R13,
h) —($C_4$-$C_{14}$)-heteroaryl, wherein heteroaryl is unsubstituted or mono-, di-, tri- or four times substituted independently of one another by R13,
i) —($C_3$-$C_8$)-cycloalkyl, wherein said cycloalkyl is unsubstituted or mono-, di-, tri- or four times substituted independently of one another by R13,
j) a 3- to 7-membered cyclic residue, containing 1, 2, 3 or 4 heteroatoms chosen from nitrogen, sulphur or oxygen, wherein said cyclic residue is unsubstituted or mono-, di-, tri- or four times substituted independently of one another by R13,
k) —O—$CF_3$,
l) —O—($C_1$-$C_4$)-alkyl, wherein alkyl is unsubstituted or substituted one to three times by R13,
m) —$NO_2$,
n) —CN,
o) —OH,
p) —C(O)—R10,
q) —C(O)—O—R11,
r) —C(O)—N(R11)-R12,
s) —N(R11)-R12,
t) —N(R10)-$SO_2$—R10,
v) —S—R10,
w) —$SO_n$—R10, wherein n is 1 or 2,
x) —$SO_2$—N(R11)-R12 or
R1 and R2, R2 and R3 or R3 and R4 form together with the atoms which they are attached to a 5- or 8-membered ring, containing up to 0, 1, 2, 3 or 4 heteroatoms chosen from nitrogen, sulphur or oxygen, wherein said ring is unsubstituted or substituted one, two, three or four times by R14,
R10 is hydrogen atom, —($C_1$-$C_3$)-fluoroalkyl or —($C_1$-$C_6$)-alkyl,
R11 and R12 are independently of one another identical or different and are
a) hydrogen atom,
b) —($C_1$-$C_6$)-alkyl, wherein alkyl is unsubstituted or mono-, di- or trisubstituted independently of one another by R13,
c) —($C_6$-$C_{14}$)-aryl-, wherein aryl is unsubstituted or mono-, di- or trisubstituted independently of one another by R13,
d) —($C_4$-$C_{14}$)-heteroaryl, wherein heteroaryl is unsubstituted or mono-, di- or trisubstituted independently of one another by R13 or
R13 is halogen, —$NO_2$, —CN, =O, —OH, —($C_1$-$C_8$)-alkyl, —($C_1$-$C_8$)-alkoxy, —$CF_3$, phenyloxy-, —C(O)—R10, —C(O)—O—R17, —C(O)—N(R17)-R18, —N(R17)-R18, —N(R10)-$SO_2$—R10, —S—R10, —$SO_n$—R10, wherein n is 1 or 2, —$SO_2$—N(R17)-R18, —($C_6$-$C_{14}$)-aryl, wherein aryl is unsubstituted or mono-, di- or trisubstituted independently of one another by R14, —($C_4$-$C_{14}$)-heteroaryl, wherein heteroaryl is unsubstituted or mono-, di- or trisubstituted independently of one another by R14, —($C_3$-$C_8$)-cycloalkyl, wherein said cycloalkyl is unsubstituted or mono-, di- or trisubstituted independently of one another by R14, or a 3- to 7-membered cyclic residue, containing up to 1, 2, 3 or 4 heteroatoms chosen from nitrogen, sulphur or oxygen, wherein said cyclic residue is unsubstituted or mono-, di- or trisubstituted independently of one another by R14, R14 is halogen, —OH, =O, —CN, —$CF_3$, —($C_1$-$C_8$)-alkyl, —($C_1$-$C_4$)-alkoxy, —$NO_2$, —C(O)—OH, —$NH_2$, —C(O)—O—($C_1$-$C_4$)-alkyl, —($C_1$-$C_8$)-alkylsulfonyl, —C(O)—NH—($C_1$-$C_8$)-alkyl, —C(O)—N[($C_1$-$C_8$)-alkyl]$_2$, —C(O)—$NH_2$, —S—R10, —N(R10)—C(O)—NH—($C_1$-$C_8$)-alkyl, or —N(R10)-C(O)—N[($C_1$-$C_8$)-alkyl]$_2$,
R17 and R18 are independently of one another identical or different and are
a) hydrogen atom,
b) —($C_1$-$C_6$)-alkyl,
c) —($C_6$-$C_{14}$)-aryl- or
d) —($C_4$-$C_{14}$)-heteroaryl,
said process comprises reacting a compound of formula II

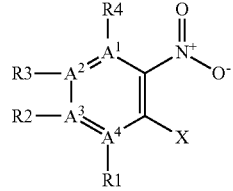

(II)

wherein R1, R2, R3, R4, A1, A2, A3 and A4 are as defined in formula I and
X is Cl, Br, I, triflate or nonaflate, with a compound of formula III

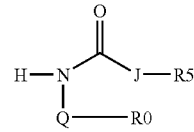

(III)

wherein Q, J, R0 and R5 are as defined in formula I,
in the presence of a copper catalyst, a base, a ligand, wherein the ligand is selected from the group consisting of 1,3-propylenediamine, 1,2-benzenediamine, phenanthridine, acridine, acridine orange, 9-aminoacridine, 9-hydroxy-4-methoxyacridine, proflavine, 4-(2-pyridylazo) resorcinol, 1,2-dihydro-1-(2-(2-pyridyl)-ethyl)-3, 6-pyridazinedione, [1,10]phenanthroline, 5-nitro-[1,10] phenanthroline, bathophenanthroline, spiramycin, bicinchonic acid sodium salt (bca), 1-(4-pyridyl) pyridinium chloride, 2-pyridylacetic acid hydrochloride, 8-mercaptoquinoline hydrochloride, dimethylamino acetic acid, picolinic acid, 3-hydroxypicolinic acid, 3-hydroxy picolinamide, pyridine, 2-aminopyridine, 2-hydroxypyridine, 3-cyano-pyridine, 4-cyanopyridine, 2-ethylpyridine, 2-amino-6-methylpyridine, 2-(aminomethylpyridine), 2-(hydroxymethylpyridine), 2-hydroxy-6-methylpyridine, 2-dimethylaminopyridine, 4-dymethylaminopyridine, 2-(2-hydroxyethyl)pyridine, 4-tert-butylpyridine, 3-acetoxypyridine, 2-phenylpyridine, 4-phenylpyridine, 4-benzoylpyridine, 2-(2-thienyl)pyridine, 2-benzylpyridine, 2-anilinopyridine, 3-pyridinepropanol, 1-(2-pyridyl) piperazine, di-2-pyridyl ketone, ethyl 2-pyridyl acetate, 2-(2-diethylaminoethyl)-pyridine, 4-(2-diethylaminoethyl)-pyridine, 2,6-di-tert-butyl pyridine, (S,S)-2,6-bis(4-isopropyl-2-oxazolin-2-yl) pyridine, 2,3-pyridine dicarboxylic acid, 2,6-pyridine dicarboxylic acid, 3,5-pyridine dicarboxylic acid, 1,3-di(4-pyridyl)propane, 2,3-di-3-pyridyl-2,3-butanediol, 4,4'-dimethyl-2,2'-dipyridyl, 3-hydroxypyridine, 2-mercaptopyridine, 2-(2-methylaminoethyl) pyridine, 3-hydroxy picolinamine, 3-hydroxypicolinic acid, 2,2':6',2"-terpyridine, 2-picoline, 6,6'-bi-2-picoline, 2,4-lutidine, 2,6-lutidine-α-2,3-diol, 2,6-lutidine 2,4,6-collidine, picolinamide, ethyl picolinate, ethyl isonicotinate, quinoline, 2-phenylquinoline, 8-hydroxyquinoline, 8-acetoxyquinoline, 2-methyl-8-nitroquinoline, 7,8-benzoquinoline, 2-quinolinol, 2-quinolinethiol, quinoline-4-carboxylic acid, 2-phenyl-4-quinoline carboxylic acid, 2,4-hydroxy quinoline monosodium salt, 8-ethoxyquinoline-5-sulfonic acid sodium salt, 8-hydroxy-5-nitroquinoline, 4-chloro-7-(trifluoromethyl) quinoline, 8-hydroxyquinoline-5-sulfonic acid monohydrate, 5-nitroquinaldic acid, isoquinoline, isoquinoline-3-carboxylic acid hydrate, 1,4,5-triazanaphtalene, quinaldine, 4-chloroquinaldine, nicotine, isonicotinamine or neocuproine, and an aprotic solvent, wherein the aprotic solvent is selected from the group consisting of benzene, toluene, xylene, mesitylene, acetonitrile, tetrahydrofurane, dimethylformamide, n-methylpyrrolodinone, dimethylacetamide, dimethylsulfoxide, (2-methoxyethyl)ether and pyridine in the temperature range from 60 ° C. to 150 ° C. to give a compound of formula IV

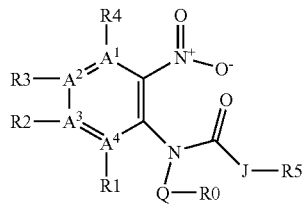

(IV)

and converting the compound of formula IV into a compound of formula I in the presence of a reducing reagent and a second solvent, wherein the second solvent is selected from the group consisting of methanol, ethanol, propanol, acetic acid, methylene chloride, dimethylformamide, tetrahydrofurane, pyridine, p-xylene, ethylacetate, benzene, toluene, xylene, mesitylene and acetonitrile in the temperature range from 80 ° C. to 140 ° C.

and optionally the compound of formula I is converted to its physiologically tolerated salt.

2. The process according to claim 1, wherein a compound of formula I is prepared, wherein A1, A2, A3 and A4 form together with the carbon atoms they are attached to a stable aromatic or heteroaromatic ring selected from benzene, pyrazine, pyridazine, pyridine, pyrimidine, triazine or tetrazine;

Q is —($C_1$-$C_6$)-alkylene, wherein alkylene is unsubstituted or mono-, di- or trisubstituted independently of one another by R14;

—($C_3$-$C_6$)-cycloalkyl, wherein cycloalkyl is unsubstituted or mono-, di- or trisubstituted independently of one another by R14;

phenyl, wherein phenyl is unsubstituted or mono-, di-, tri- or four times substituted independently of one another by R13: or —($C_4$-$C_{14}$)-heteroaryl, wherein heteroaryl is selected from acridinyl, azaindole (1H-pyrrolopyridinyl), azabenzimidazolyl, azaspirodecanyl, azepinyl, azetidinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyrazolo[3,4-b]pyridine, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein heteroaryl is unsubstituted or mono-, di-, tri- or four times substituted independently of one another by R13;

J is a covalent bond,

—($C_1$-$C_6$)-alkylene, wherein alkylene is unsubstituted or mono-, di- or trisubstituted independently of one another by R14;

—($C_2$-$C_6$)-alkenylene, wherein alkenylene is unsubstituted or mono-, di- or trisubstituted independently of one another by R14, —($C_3$-$C_6$)-cycloalkyl, wherein cycloalkyl is unsubstituted or mono-, di- or trisubstituted independently of one another by R14;

phenyl, wherein phenyl is unsubstituted or mono-, di-, tri- or four times substituted independently of one another by R13: or —($C_4$-$C_{14}$)-heteroaryl, wherein heteroaryl is as defined above and is unsubstituted or mono-, di-, tri- or four times substituted independently of one another by R13;

R0, R1, R2, R3, R4 and R5 are independent of one another identical or different and are a) hydrogen atom, b) F, c) Cl or Br, d) —($C_1$-$C_4$)-alkyl, wherein alkyl is unsubstituted or substituted one to three times by R13, e) —($C_1$-$C_3$)-fluoroalkyl, f) phenyl, wherein phenyl is unsubstituted or substituted one to three times by R13, g) —($C_4$-$C_{14}$)-heteroaryl, wherein heteroaryl is as defined above and is unsubstituted or mono-, di-, tri- or four times substituted independently of one another by R13, h) —($C_3$-$C_8$)-cycloalkyl, wherein said cycloalkyl is unsubstituted or mono-, di-, tri- or four times substituted independently of one another by R13, i) a 3- to 7-membered cyclic residue selected from azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyrazolo-[3,4-b]pyridine, pyridazine, pyridine, pyrimidine, pyrrole, pyrrolidine, pyrrolidinone, pyrroline, tetrahydrofuran, tetrahydropyran, tetrahydro-pyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, and is unsubstituted or mono-, di-, tri- or four times substituted independently of one another by R13, j) —O—CF$_3$, k) —O—(C$_1$-C$_4$)-alkyl, wherein alkyl is unsubstituted or substituted one to three times by R13, l) —N(R10)-(C$_1$-C$_4$)-alkyl, wherein alkyl is unsubstituted or substituted one to three times by R13, m) —CN, n) —OH, o) phenyloxy-, wherein phenyloxy is unsubstituted or substituted one to three times by R13, p) —C(O)—O—R11, q) —C(O)—N(R11)-R12, r) —N(R11)-R12, s) —N(R10)-SO$_2$—R10, t) —S—R10, v) —SO$_n$—R10, wherein n is 1 or 2, w) —SO$_2$—N(R11)-R12, x) —C(O)—R10 or R10 is hydrogen atom, —(C$_1$-C$_3$)-fluoroalkyl or —(C$_1$-C$_6$)-alkyl, R11 and R12 are independently of one another identical or different and are a) hydrogen atom, b) —(C$_1$-C$_4$)-alkyl, wherein alkyl is unsubstituted or mono-, di- or trisubstituted independently of one another by R13, c) phenyl, wherein phenyl is unsubstituted or mono-, di- or trisubstituted independently of one another by R13, d) —(C$_4$-C$_{14}$)-heteroaryl, wherein heteroaryl is as defined above and is unsubstituted or mono-, di- or trisubstituted independently of one another by R13 or R13 is F, Cl, —CN, =O, —OH, —(C$_1$-C$_8$)-alkyl, —(C$_1$-C$_8$)-alkoxy, —CF$_3$, phenyloxy-, —C(O)—R10, —C(O)—O—R17, —C(O)—N(R17)-R18, —N(R17)-R18, —N(R10)-SO$_2$—R10, —S—R10, —SO$_n$—R10, wherein n is 1 or 2, —SO$_2$—N(R17)-R18, phenyl, wherein phenyl is unsubstituted or mono-, di- or trisubstituted independently of one another by R14, —(C$_4$-C$_{14}$)-heteroaryl, wherein heteroaryl is as defined above and is unsubstituted or mono-, di- or trisubstituted independently of one another by R14, —(C$_3$—C$_6$)-cycloalkyl, wherein said cycloalkyl is unsubstituted or mono-, di- or trisubstituted independently of one another by R14, or a 3- to 7-membered cyclic residue, which is as defined above and is unsubstituted or mono-, di- or trisubstituted independently of one another by R14, R14 is F, Cl, —OH, =O, —CN, —CF$_3$, —(C$_1$-C$_8$)-alkyl, —(C$_1$-C$_4$)-alkoxy, —C(O)—OH, —NH$_2$, —C(O)—O—(C$_1$-C$_4$)-alkyl, —(C$_1$-C$_8$)-alkylsulfonyl, —C(O)—NH$_2$, —C(O)—NH—(C$_1$-C$_8$)-alkyl, —C(O)—N[(C$_1$-C$_8$)-alkyl]$_2$, —S—R10, —N(R10)-C(O)—NH—(C$_1$-C$_8$)-alkyl or —N(R10)-C(O)—N[(C$_1$-C$_8$)-alkyl]$_2$, R17 and R18 are independently of one another identical or different and are a) hydrogen atom, b) —(C$_1$-C$_4$)-alkyl, c) phenyl or d) —(C$_4$-C$_{14}$)-heteroaryl and X is Cl, Br or I.

3. The process according to claim 1, wherein a compound of formula I is prepared, wherein A1, A2, A3 and A4 form together with the carbon atoms they are attached to a stable aromatic or heteroaromatic ring selected from benzene or pyridine, Q is phenyl, J is a covalent bond, —(C$_1$-C$_6$)-alkylene, wherein alkylene is unsubstituted or mono-, di- or trisubstituted independently of one another by R14; phenyl or pyridyl;

R0, R1, R2, R3, R4 and R5 are independent of one another identical or different and are a) hydrogen atom, b) F, c) Cl, d) Br, e) —(C$_1$-C$_4$)-alkyl, f) —O—(C$_1$-C$_4$)-alkyl, g) —C(O)—O—R11, h) —S—R10, i) —C(O)—R10 or R10 is hydrogen atom or —(C$_1$-C$_4$)-alkyl, R11 is a) hydrogen atom, or b) —(C$_1$-C$_4$)-alkyl, R14 is —(C$_1$-C$_8$)-alkyl or —C(O)—O—(C$_1$-C$_4$)-alkyl, and X is Cl, Br or I.

4. The process according to claim 1, wherein one of the following compounds of formula I is prepared:

2-Methyl-1-phenyl-1H-benzimidazole; 5-Chloro-2-methyl-1-phenyl-1H-benzimidazole; 2,7-Dimethyl-1-phenyl-1H-benzimidazole; 5-Methoxy-2-methyl-1-phenyl-1H-benzimidazole; 2-Methyl-1-phenyl-1H-benzimidazole-5-carboxylic acid methyl ester; 2-Methyl-1-phenyl-1H-benzimidazole-5-carbaldehyde; 1,2-Diphenyl-1H-benzimidazole; 1-Phenyl-2-pyridin-3-yl-1H-benzimidazole; 1-Phenyl-2-tridecyl-1H-benzimidazole; 5-(1-Phenyl-1H-benzoimidazol-2-yl)-pentanoic acid methyl ester; 1-(4-Methoxy-phenyl)-2-methyl-1H-benzimidazole; 2,4-Dimethyl-1-phenyl-1H-benzimidazole; 1-(2-Methoxy-phenyl)-2-methyl-1H-benzoimidazole; 1-(2-Chloro-phenyl)-2-methyl-1H-benzoimidazole; 2-Methyl-1-(4-methylsulfanylphenyl)-1H-benzoimidazole; 1-(4-Bromo-phenyl)-2-methyl-1H-benzoimidazole, 2,4-Dimethyl-1-phenyl-1H-benzoimidazole-5-carboxylic acid methyl ester; 5-Fluoro-2-methyl-1-phenyl-1H-benzoimidazole; 5-Bromo-2-methyl-1-phenyl-1H-benzoimidazole; 1-(2-Methyl-1-phenyl-1H-benzoimidazol-5-yl)-ethanone; 6-Fluoro-2-methyl-1-phenyl-1H-benzoimidazole; 1-Phenyl-1H-benzoimidazole; 6-Methoxy-1-phenyl-1H-benzoimidazole; 2-Methyl-3-phenyl-3H-benzoimidazole-4-carboxylic acid methyl ester; 2-Methyl-1-phenyl-1H-imidazo[4,5-b]pyridine; 2-Methyl-3-phenyl-3H-imidazo[4,5-b]pyridine;

5-Methoxy-2-methyl-3-phenyl-3H-imidazo[4,5-b]pyridine; 3-(1-Phenyl-1H-benzimidazol-2-yl)-propionic acid ethyl ester; 1-(2-Chloro-phenyl)-2-((E)-styryl)-1H-benzimidazole or 2,5-Dimethyl-3-phenyl-3H-imidazo[4,5-b]pyridine.

5. The process according to claim 1, wherein the copper catalyst is selected from:
copper (I) chloride, copper (I) bromide, copper (I) iodide and copper (I) oxide.

6. The process according to claim 5, wherein the copper catalyst is copper (I) iodide.

7. The process according to claim 1, wherein the base is selected from the group consisting of carbonates, phosphates, fluorides, alkoxides and hydroxides with a suitable metal as counterion.

8. The process according to claim 7, wherein the base is selected from the group consisting of potassium carbonate, potassium phosphate and caesium carbonate.

9. The process according to claim 1, wherein the reaction between the compound of formula II and formula III is carried out in the temperature range from from 90° C. to 110° C.

10. The process according to claim 1, wherein the reducing reagent is selected from the group consisting of $H_2$/Raney-Ni, $H_2$/Pd—C, $H_2$/PtO$_2$, $H_2$/Ru, NaBH$_4$/NiCl$_2$, NaBH$_4$/FeCl$_2$, $H_3PO_2$/Pd—C, Sn/HCl, SnCl$_2$/HCl, Fe/HOAc, Fe/HCl, FeSO$_4$/HCl, Fe/FeSO$_4$, Zn/HCl, Na$_2$S, and Na$_2$S$_2$O$_4$.

11. The process according to claim 1, wherein the reduction reaction of the compound of formula IV to the compound of formula I is carried out in the temperature range from 110° C. to 120° C.

12. The process according to claim 1 wherein the ligand is selected from the group consisting of phenanthridine, acridine, acridine orange, 9-aminoacridine, 9-hydroxy-4-methoxyacridine, proflavine, 4-(2-pyridylazo) resorcinol, 1,2-dihydro-1-(2-(2-pyridyl)-ethyl)-3,6-pyridazinedione, [1,10] phenanthroline, 5-nitro-[1,10]phenanthroline, bathophenanthroline, spiramycin, bicinchonic acid sodium salt (bca), 1-(4-pyridyl) pyridinium chloride, 2-pyridylacetic acid hydrochloride, 8-mercaptoquinoline hydrochloride, dimethylamino acetic acid, picolinic acid, 3-hydroxypicolinic acid, 3-hydroxy picolinamide, pyridine, 2-aminopyridine, 2-hydroxypyridine, 3-cyano-pyridine, 4-cyanopyridine, 2-ethylpyridine, 2-amino-6-methylpyridine, 2-(aminomethylpyridine), 2-(hydroxymethylpyridine), 2-hydroxy-6-methylpyridine, 2-dimethylaminopyridine, 4-dymethylaminopyridine, 2-(2- hydroxyethyl) pyridine, 4-tert-butylpyridine, 3-acetoxypyridine, 2-phenylpyridine, 4-phenylpyridine, 4-benzoylpyridine, 2-(2-thienyl)pyridine, 2-benzylpyridine, 2-anilinopyridine, 3-pyridinepropanol, 1-(2-pyridyl) piperazine, di-2-pyridyl ketone, ethyl 2-pyridyl acetate, 2-(2-diethylaminoethyl)-pyridine, 4-(2-diethylaminoethyl)-pyridine, 2,6-di-tert-butyl pyridine, (S,S)-2,6-bis(4-isopropyl-2-oxazolin-2-yl) pyridine, 2,3-pyridine dicarboxylic acid, 2,6-pyridine dicarboxylic acid, 3,5-pyridine dicarboxylic acid, 1,3-di(4-pyridyl)propane, 2,3-di-3-pyridyl-2,3-butanediol, 4,4'-dimethyl-2,2'-dipyridyl, 3-hydroxypyridine, 2-mercaptopyridine, 2-(2-methylaminoethyl) pyridine, 3-hydroxy picolinamine, 3-hydroxypicolinic acid, 2,2':6',2"-terpyridine, 2-picoline, 6,6'-bi-2-picoline, 2,4-lutidine, 2,6-lutidine-α-2,3-diol, 2,6-lutidine 2,4,6-collidine, picolinamide, ethyl picolinate, ethyl isonicotinate, quinoline, 2-phenylquinoline, 8-hydroxyquinoline, 8-acetoxyquinoline, 2-methyl-8-nitroquinoline, 7,8-benzoquinoline, 2-quinolinol, 2-quinolinethiol, quinoline-4-carboxylic acid, 2-phenyl-4-quinoline carboxylic acid, 2,4-hydroxy quinoline monosodium salt, 8-ethoxyquinoline-5-sulfonic acid sodium salt, 8-hydroxy-5-nitroquinoline, 4-chloro-7-(trifluoromethyl) quinoline, 8-hydroxyquinoline-5-sulfonic acid monohydrate, 5-nitroquinaldic acid, isoquinoline, isoquinoline-3-carboxylic acid hydrate, 1,4,5-triazanaphtalene, quinaldine, 4-chloroquinaldine, nicotine, isonicotinamine and neocuproineine.

\* \* \* \* \*